United States Patent
Mezrich et al.

(10) Patent No.: US 11,478,326 B2
(45) Date of Patent: Oct. 25, 2022

(54) SURGICAL LIGHT AND USES THEREOF

(71) Applicant: MezLight, LLC, Madison, WI (US)

(72) Inventors: Joshua David Mezrich, Madison, WI (US); Craig James Christianson, Madison, WI (US); Christopher Charles Beglinger, Madison, WI (US)

(73) Assignee: MezLight, LLC, Madison, WI (US)

( * ) Notice: Subject to any disclaimer, the term of this patent is extended or adjusted under 35 U.S.C. 154(b) by 0 days.

(21) Appl. No.: 16/926,085

(22) Filed: Jul. 10, 2020

(65) Prior Publication Data

US 2020/0337796 A1    Oct. 29, 2020

Related U.S. Application Data

(63) Continuation-in-part of application No. 15/978,954, filed on May 14, 2018, now abandoned.

(Continued)

(51) Int. Cl.
| | | |
|---|---|---|
| *A61B 90/35* | (2016.01) | |
| *A61B 90/57* | (2016.01) | |
| *A61B 90/00* | (2016.01) | |
| *A61B 90/30* | (2016.01) | |
| *F21K 9/20* | (2016.01) | |
| *F21V 21/32* | (2006.01) | |

(Continued)

(52) U.S. Cl.
CPC ............ *A61B 90/35* (2016.02); *A61B 90/361* (2016.02); *A61B 90/57* (2016.02); *A61B 1/06* (2013.01); *A61B 90/30* (2016.02); *A61B 2090/308* (2016.02); *A61B 2090/571* (2016.02); *F21K 9/20* (2016.08); *F21V 21/088* (2013.01); *F21V 21/28* (2013.01); *F21V 21/32* (2013.01); *F21Y 2107/70* (2016.08)

(58) Field of Classification Search
CPC ... A61B 90/30; A61B 90/35; A61B 2090/306; A61B 2090/308; A61B 2090/309; A61B 1/0684; A61B 1/06; A61B 1/0638; A61B 1/0661; A61B 1/233; A61B 1/227; F21Y 2115/10; F21Y 2107/70; F21V 21/14; F21V 21/32; F21V 21/08; F21V 21/088; F21V 21/28; F21K 9/20; F21S 6/003; F21S 6/006
USPC ......... 362/572, 33, 573–574, 804, 581, 189, 362/197–198, 249.01–249.5, 362/249.07–249.8; 600/178–182, 249; 606/166
See application file for complete search history.

(56) References Cited

U.S. PATENT DOCUMENTS

| | | |
|---|---|---|
| 3,992,618 A | 11/1976 | Matthews et al. |
| 4,630,185 A | 12/1986 | Copeland et al. |
| | (Continued) | |

FOREIGN PATENT DOCUMENTS

JP      2007282920 A      11/2007

OTHER PUBLICATIONS

International Search Report & Written Opinion, International Patent Application No. PCT/US2018/032561, dated Aug. 6, 2018, 11 pages.

(Continued)

*Primary Examiner* — Marcela I. Shirsat
(74) *Attorney, Agent, or Firm* — Casimir Jones, S.C.; Tanya A. Arenson

(57) ABSTRACT

Provided herein are surgical lighting devices, systems, and methods. In particular, provided herein are sterile surgical lights and uses thereof.

16 Claims, 32 Drawing Sheets

Related U.S. Application Data

(60) Provisional application No. 62/505,595, filed on May 12, 2017.

(51) Int. Cl.
*F21V 21/088* (2006.01)
*F21V 21/28* (2006.01)
*F21Y 107/70* (2016.01)
*A61B 1/06* (2006.01)

(56) References Cited

U.S. PATENT DOCUMENTS

| | | | | |
|---|---|---|---|---|
| 5,115,307 | A | * | 5/1992 | Cooper .............. A61B 1/00091 348/66 |
| 5,916,214 | A | | 6/1999 | Cosio et al. |
| 6,086,228 | A | * | 7/2000 | McGowan ............ F21V 21/088 359/802 |
| 7,322,716 | B1 | * | 1/2008 | Atkinson .................. F21L 4/04 362/198 |
| 8,409,082 | B2 | * | 4/2013 | Irion ........................ A61B 1/07 600/178 |
| 9,206,951 | B2 | * | 12/2015 | McLennan .............. F21L 4/045 |
| 2003/0035301 | A1 | * | 2/2003 | Gardiner .............. A61N 5/0619 362/583 |
| 2006/0082993 | A1 | * | 4/2006 | Hsu .......................... F21S 9/02 362/197 |
| 2011/0071356 | A1 | * | 3/2011 | Edwards .......... A61B 17/32002 600/142 |
| 2014/0221754 | A1 | | 8/2014 | Cabaud et al. |
| 2015/0230697 | A1 | | 8/2015 | Phee et al. |
| 2018/0032561 | A1 | | 11/2018 | Mezrich et al. |

OTHER PUBLICATIONS

Heine EL3 LED Examination Light. Heine USA Ltd., May 23, 2016, https://www.heine.com/fileadmin/accessfiles/en_GB/download/HEINEEL31nstructionforUse.pd; accessed on Sep. 19, 2019 (Year: 2016).

* cited by examiner

SURGICAL LIGHT AND USES THEREOF

CROSS REFERENCE TO RELATED APPLICATIONS

The present invention is a continuation-in-part of U.S. patent application Ser. No. 15/978,954, which claims the priority benefit of U.S. Provisional Patent Application 62/505,595, filed May 12, 2017 which is incorporated by reference in its entirety.

FIELD

Provided herein are surgical lighting devices, systems, and methods. In particular, provided herein are sterile surgical lights and uses thereof.

BACKGROUND

Surgeons typically utilize head lamps for providing direct light during surgery. These lamps require the user to maintain an uncomfortable and static head position in order to maintain uniform lighting of the surgical field. In addition, headlamps are not typically sterile and cannot be contacted by the surgeon to adjust aim or for comfort.

Even with these significant drawbacks, head lamps are commonly used because other existing lighting systems that are mounted above the patient, on the bed frame, or elsewhere in the surgical landscape are considered ineffective in terms of intruding into the work space and/or providing insufficient, adjustable, targetable light.

Improved devices and methods for surgical lighting are needed.

SUMMARY

Provided herein are surgical lighting devices, systems, and methods. In particular, provided herein are sterile surgical lights and uses thereof.

The lighting devices, systems, and methods described herein solve many problems of the existing devices. Providing sterile devices allows users to manipulate the placement and aim of lights during procedures. This allows for better lighting of the procedure and improved comfort for the user.

For example, in some embodiments, the present disclosure provides a reusable (e.g., for 10 or more uses) or disposable, sterile, medical (e.g., surgical) light, comprising: a lamp operably linked to a multi-segment flexible arm comprising at least one rigid section and at least one flexible section. In some embodiments, the flexible arm comprises two flexible sections disposed on either side of a single rigid section. In some embodiments, the lengths of the flexible sections and the rigid section are present at a ratio of 1:2 to 2:1. In some embodiments, the light further comprises a power source (e.g., battery). In some embodiments, the light further comprises a support attachment component. In some embodiments, the support attachment component provides a component of the power source. In some embodiments, the light further comprises a camera. In some embodiments, the camera is attached to the flexible arm via a camera attachment clip. In some embodiments, the lamp is focusable. In some embodiments, the light further comprises an on-off switch. In some embodiments, the on-off switch is located on the power supply. In some embodiments, the lamp comprises at least one light source. In some embodiments, the lamp comprises at least two light sources, wherein each of the light sources emits light of a different wavelength or range of wavelengths. In some embodiments, the light source is configured to emit pulses of light. In some embodiments, the light source is configured to switch between the two light sources (e.g., as a rapid pulse).

Other embodiments provide a system, comprising: a) a sterile surgical light, comprising a lamp operably linked to a multi-segment flexible arm comprising two flexible sections disposed on either side of a single rigid section, wherein the total lengths of the flexible sections and said rigid section are present at a ratio of 0:2 to 2:1; b) a solid support configured to attach the light to a medical procedure surface using the support attachment component, wherein the solid support comprises at least two curved segments that align the surgical light over the medical procedure surface; and c) at least one electrical connector configured to attached the solid support to the sterile surgical light. In some embodiments, the electrical connector comprises one or more of an electrical contact, a locking groove and an indicator light. In some embodiments, the end of the flexible arm comprises one or more of a threaded ferrule, an electrical contact and an insertion component. In some embodiments, the insertion component is configured to insert into the electrical connector (e.g., into the locking groove).

Further embodiments provide a system, comprising: the light described herein; and a solid support configured to attach to the light using the support attachment component. In some embodiments, the solid support is sterilizable (e.g., via autoclave). In some embodiments, the solid support attaches to a medical procedure surface. In some embodiments, the solid support attaches to the medical procedure surface using a clamp. In some embodiments, the medical procedure surface is a medical or surgical procedure surface (e.g., surgical stretcher, accessory table, or surgical bed (e.g., bed rail)). In some embodiments, the height of the solid support is adjustable (e.g., via the clamp).

Yet other embodiments provide a method of lighting a medical procedure, comprising: a) contacting the system described herein with a medical procedure surface; and b) illuminating the medical procedure surface with the light. In some embodiments, the method further comprises the step of performing a medical procedure (e.g., surgery such as transplant surgery). In some embodiments, the position of the light is adjusted one or more times during the surgical procedure.

Additional embodiments are described herein.

DETAILED DESCRIPTION

Provided herein are surgical lighting devices, systems, and methods. In particular, provided herein are sterile surgical lights and uses thereof.

Figure 1:
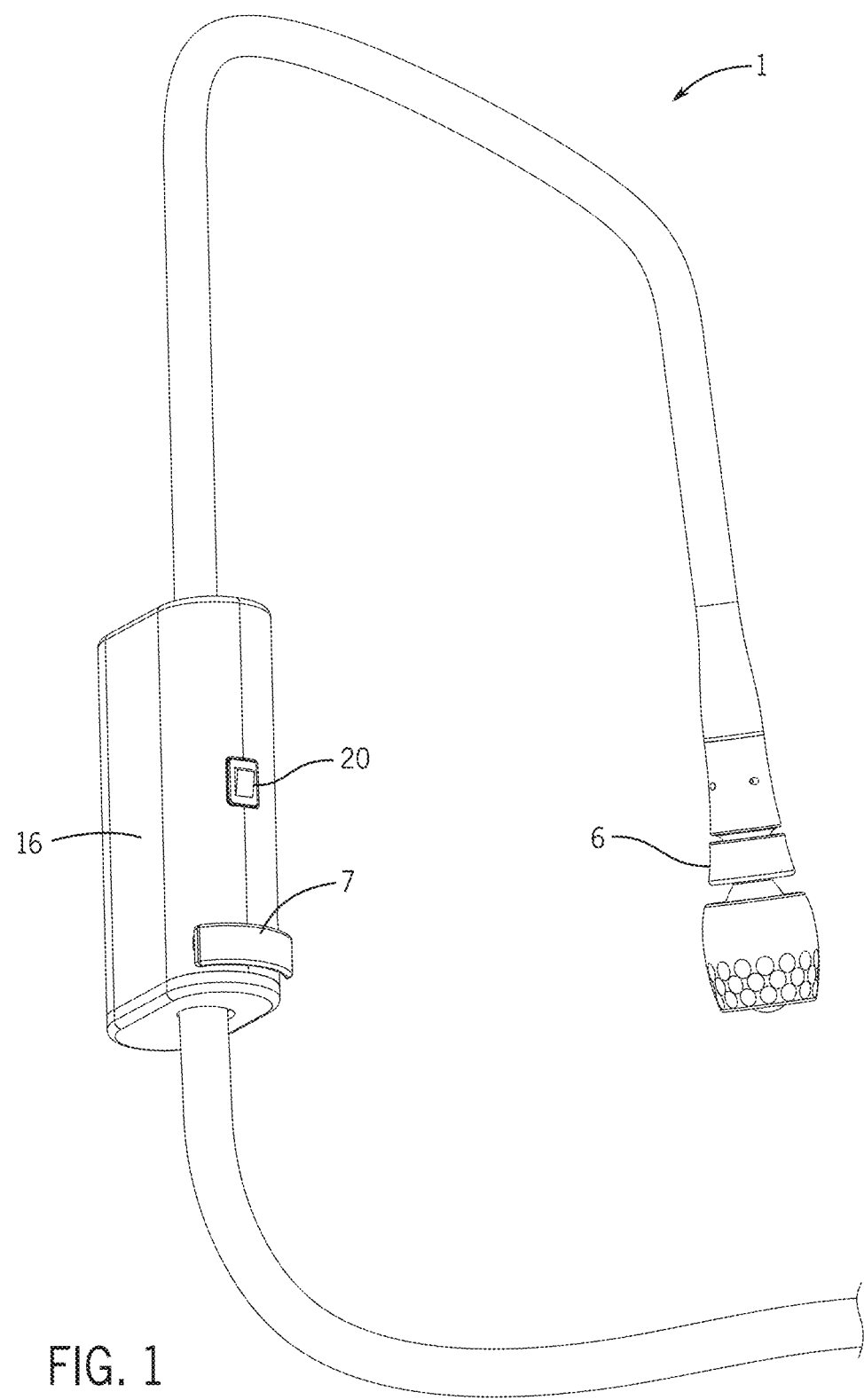
FIG. 1 shows an image of an exemplary device of embodiments of the present disclosure.
Figure 2:
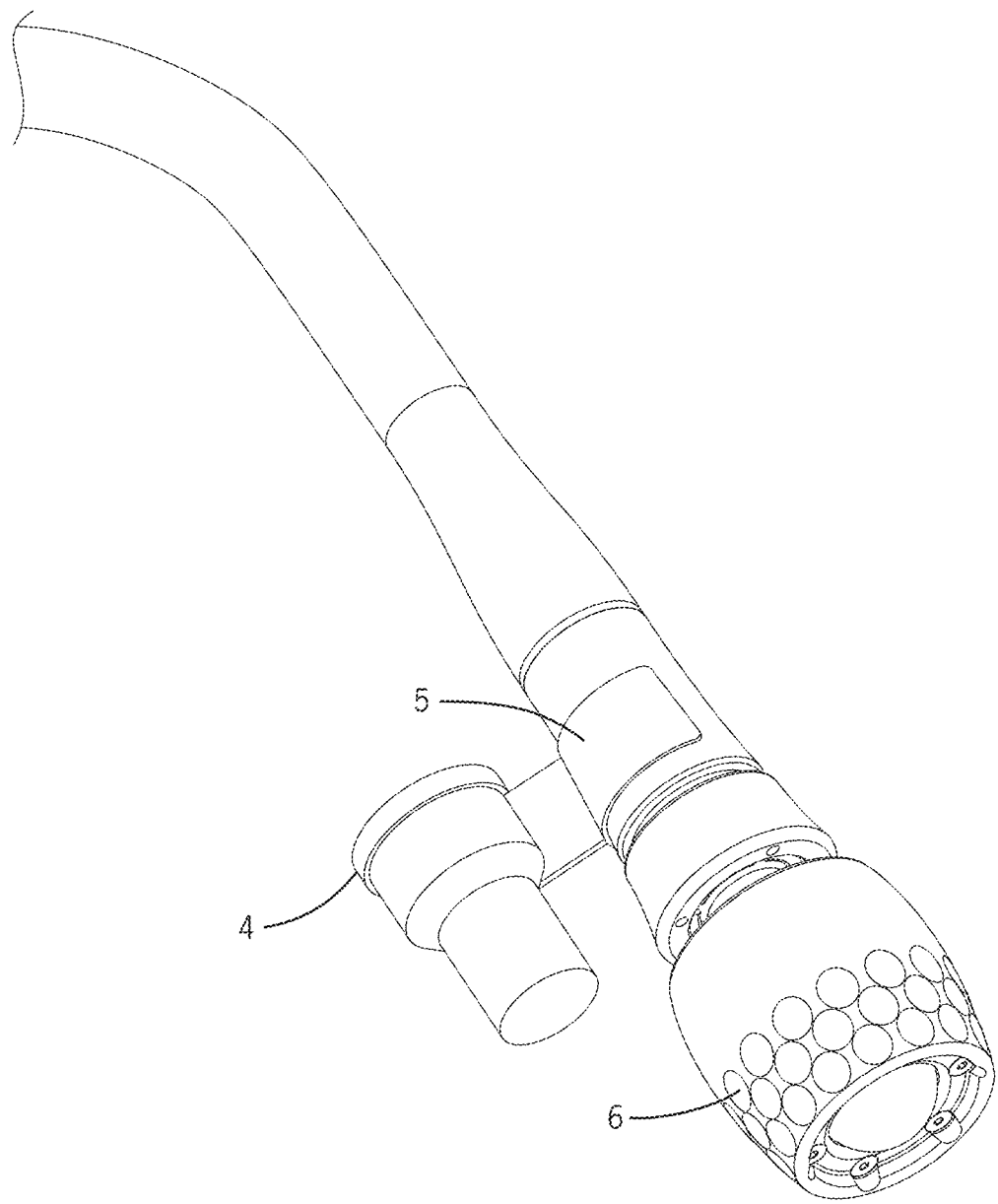
FIG. 2 shows a close-up image of an exemplary device of embodiments of the present disclosure showing a camera component.
Figure 3A:
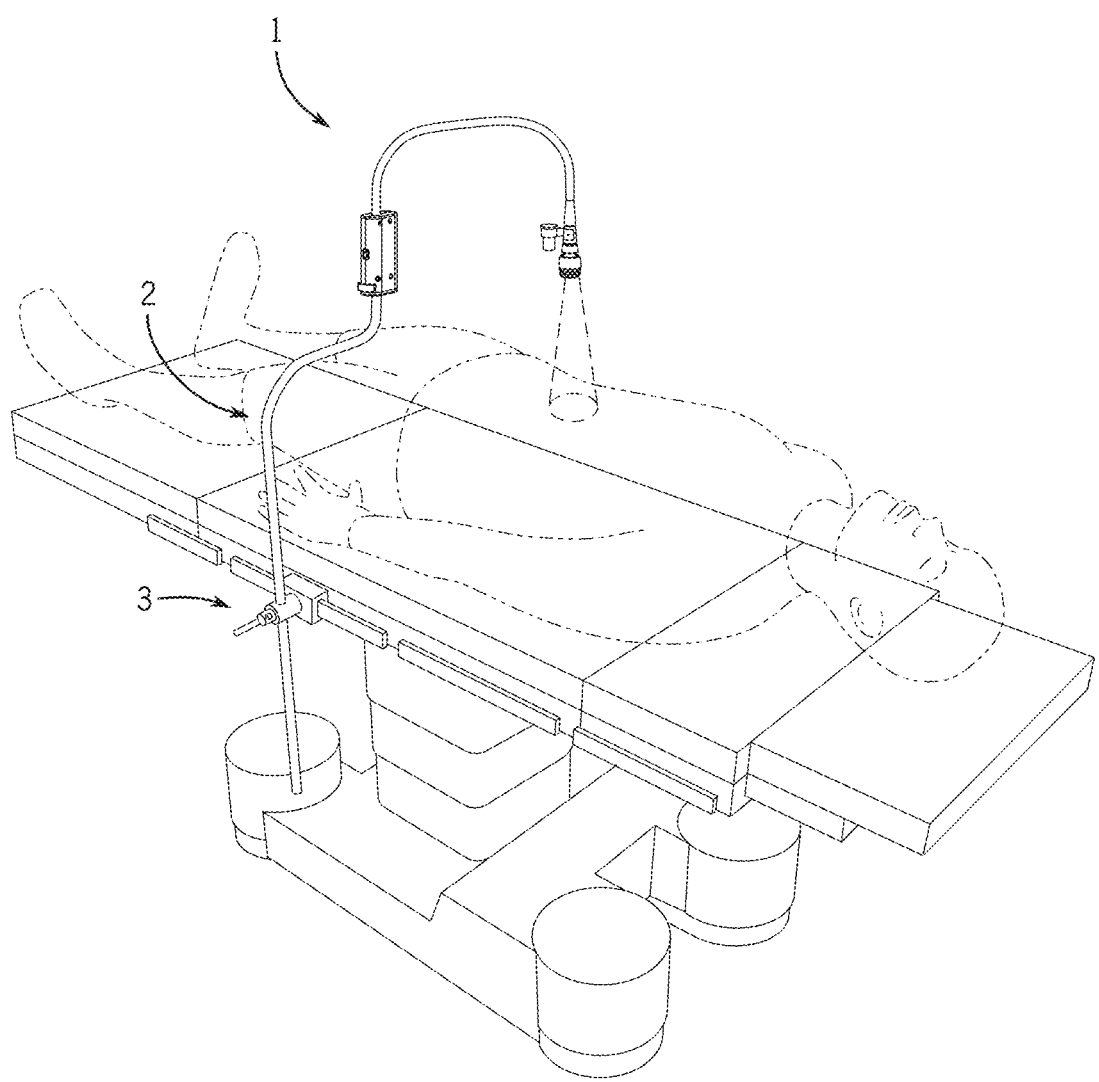
FIG. 3A-C shows an image of exemplary devices of embodiments of the present disclosure in use.
Figure 3B:
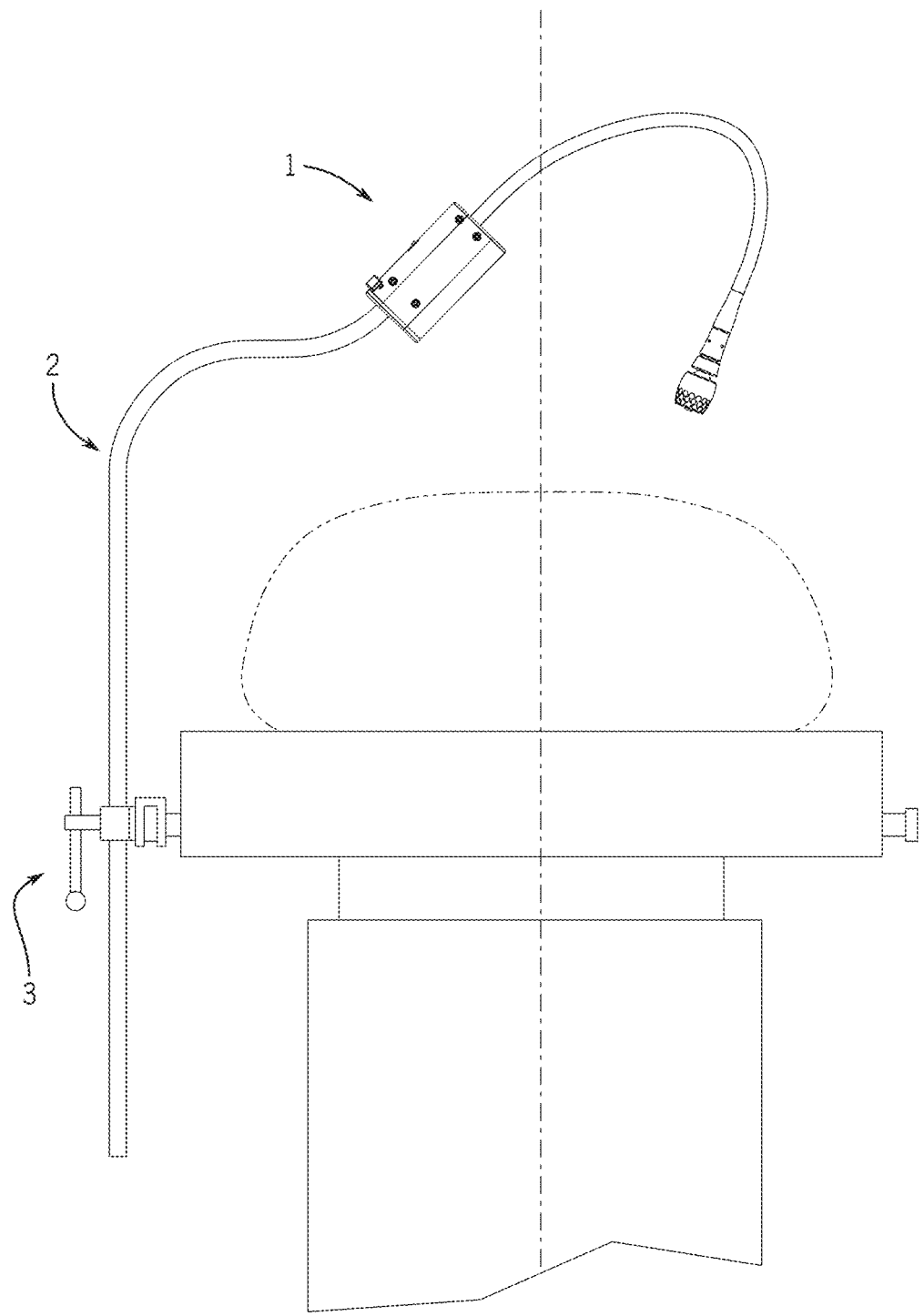
Figure 3C:
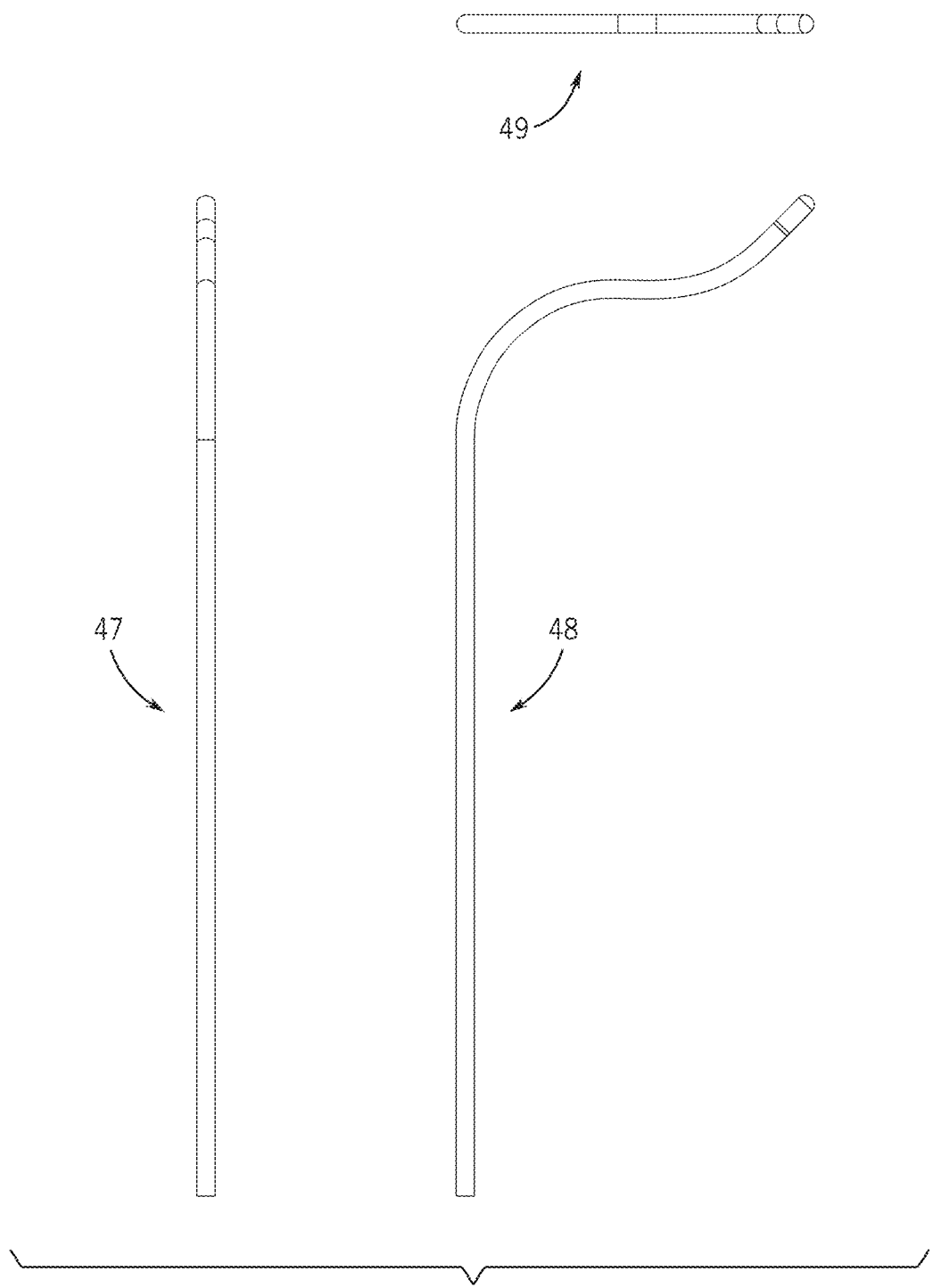

FIGS. 1-20 show exemplary devices and systems of the present disclosure. FIG. 1 shows a photograph of light 1 with lamp 6, power supply 16 with switch 20 and support attachment component 7. FIG. 2 shows a close-up image of an optional camera component 4 attached to light 1 with camera attachment clip 5. In some embodiments, camera 4 further comprises a microphone and or sound recording components (not shown). In some embodiments, a microphone is provided separately from the video camera. FIG. 3 shows an overview of the light 1 in use. Shown is light 1 attached to solid support 2. The solid support 2 is attached to a medical bed using clamp 3. FIG. 3B shows an alternative embodiment where the geometry of the support 2 is configured to aid in aligning the light 1 over the center line of the medical bed or operating table. In some embodiments, the support arm has a first, most distal segment that connects to the table or table rail, a second segment that runs approximately parallel to the plane of the table, and a third, most proximal segment, that attaches to the light component. In this embodiments, the third segment of the support arm is angled between 90° and 180° (preferably between 120° and 150°; e.g., 135°) relative to the second segment. FIG. 3C shows details of the support 2 shown in FIG. 3B, showing a back perspective 47, a side perspective 48, and a top perspective 49. In some embodiments, the support 2 comprises one or more straight or curved segments that lock together to form support 2.

Figure 4:
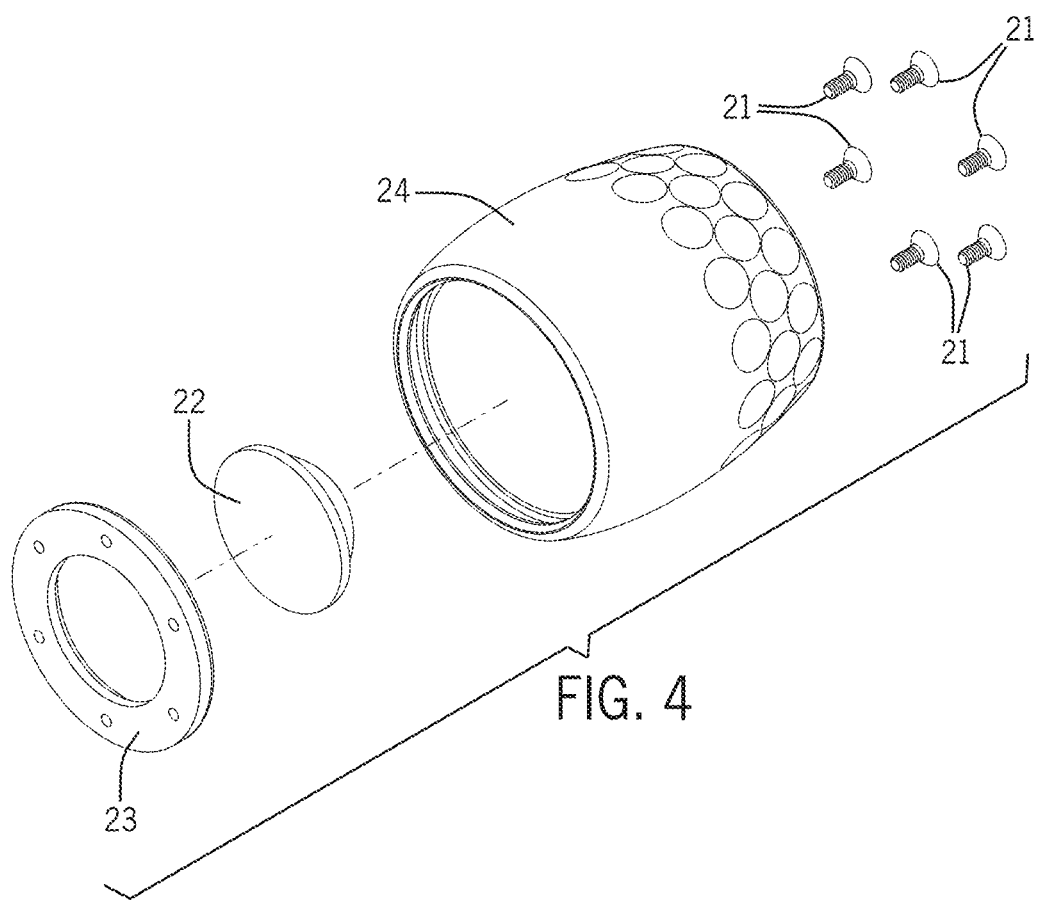
FIG. 4 shows a schematic of a lamphead assembly of an exemplary device of embodiments of the present disclosure.
Figure 5:
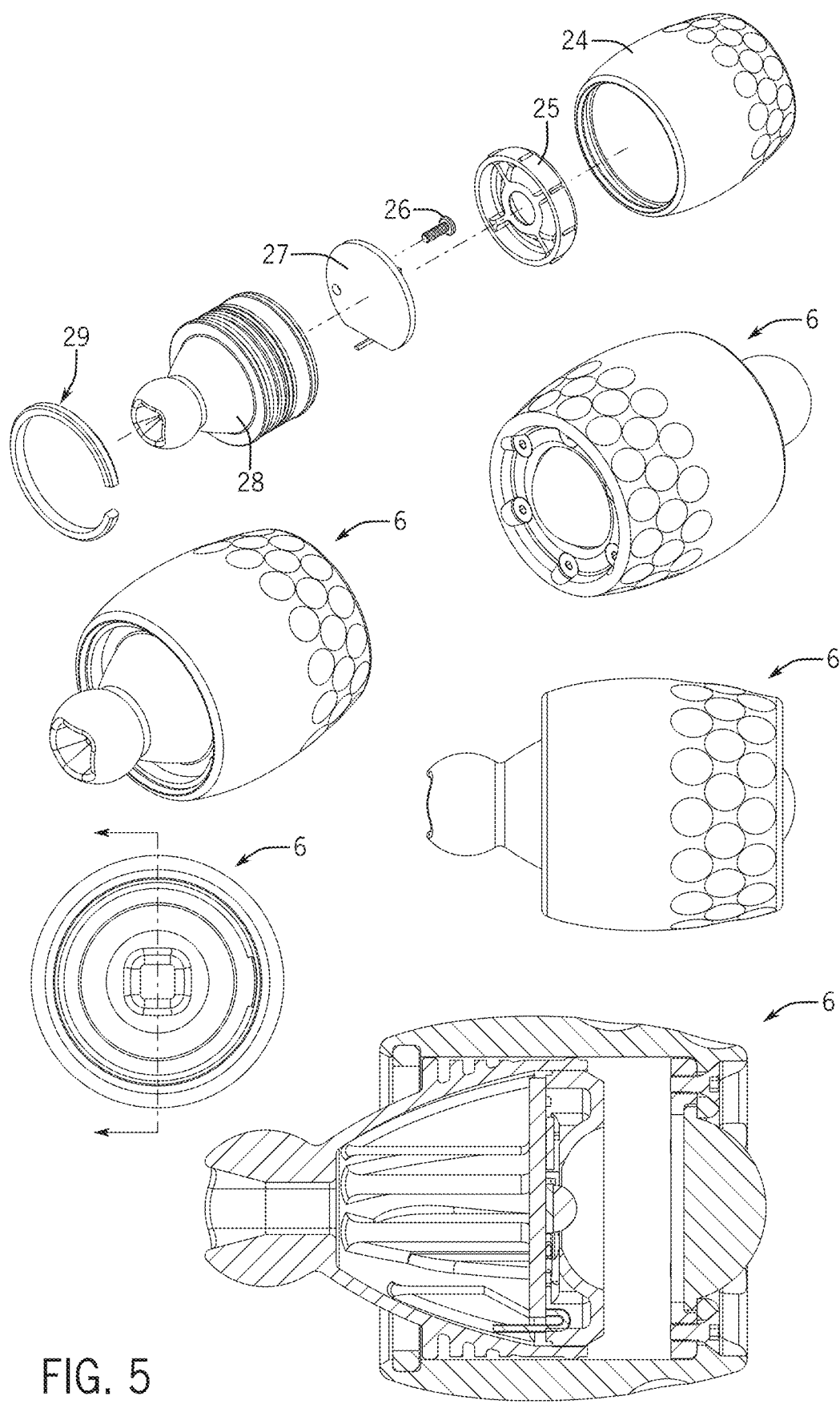
FIG. 5 shows a schematic of a lamphead assembly of an exemplary device of embodiments of the present disclosure.
Figure 6A:
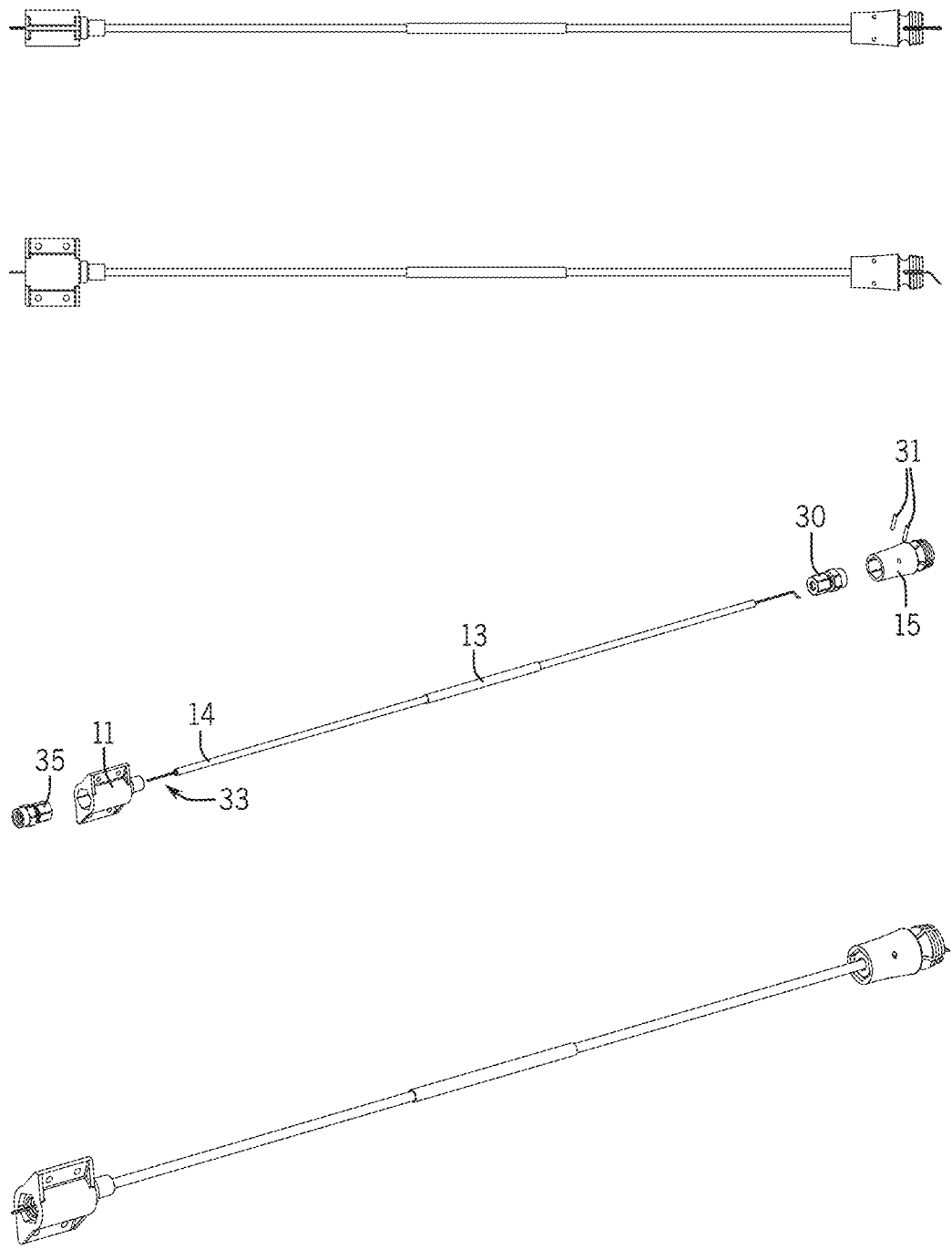
FIG. 6A-E shows a) a detail view of a flexible arm with battery connector; b) an overview of a flexible arm with battery connector; c) a flexible arm support; d) a flexible arm tube; and e) a flexible arm battery connector of an exemplary device of embodiments of the present disclosure.
Figure 6B:
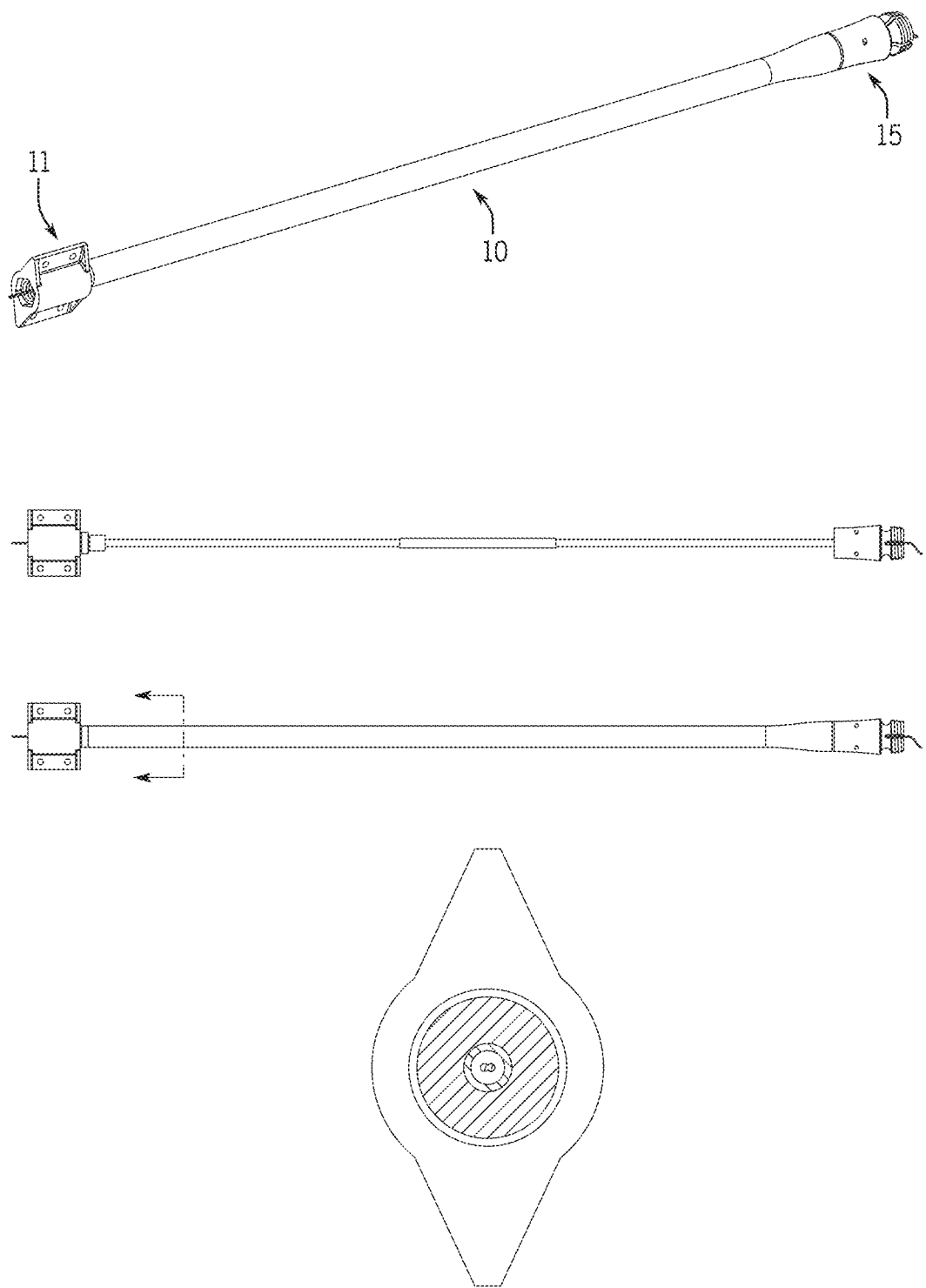
Figure 6C:
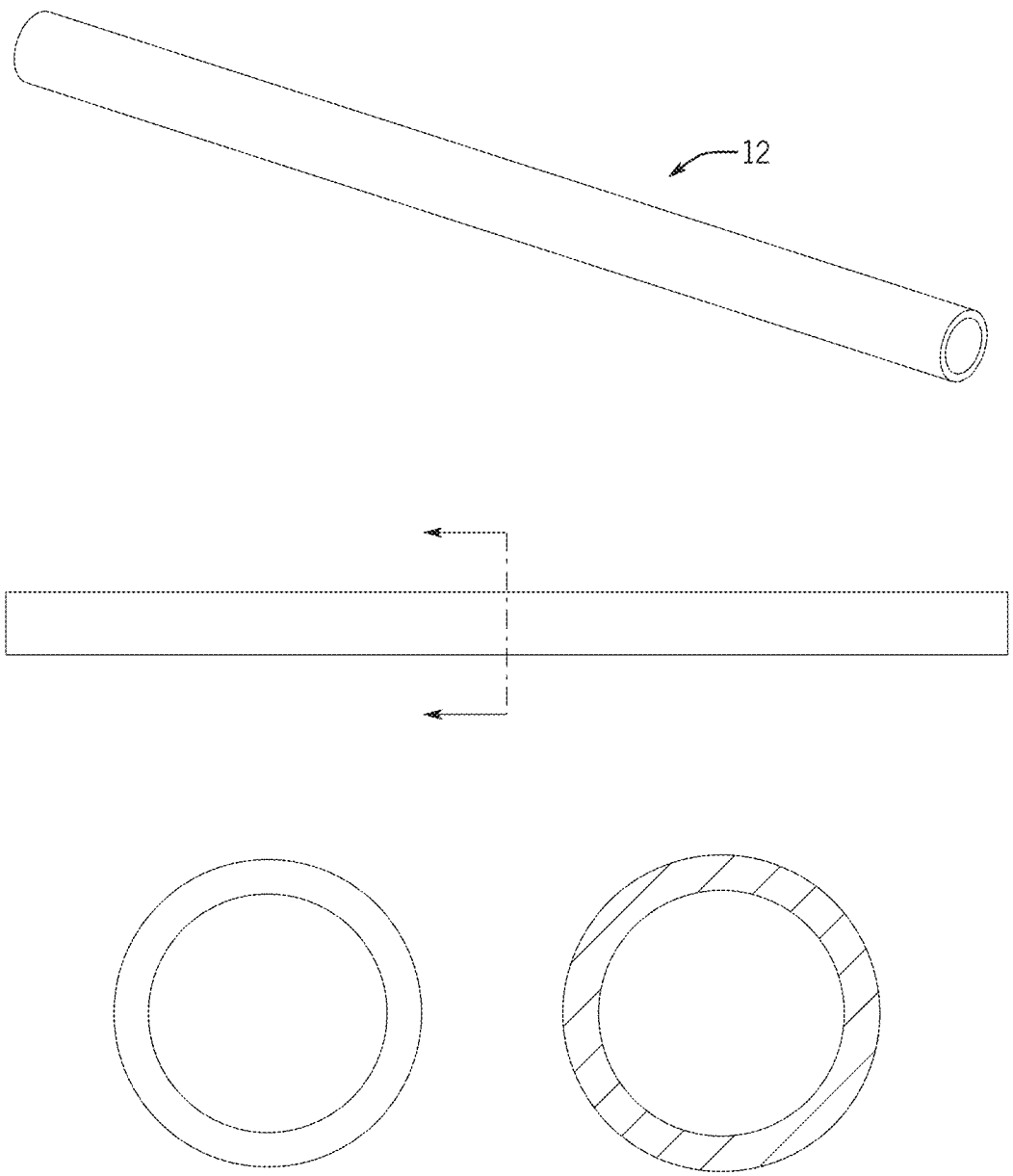
Figure 6D:
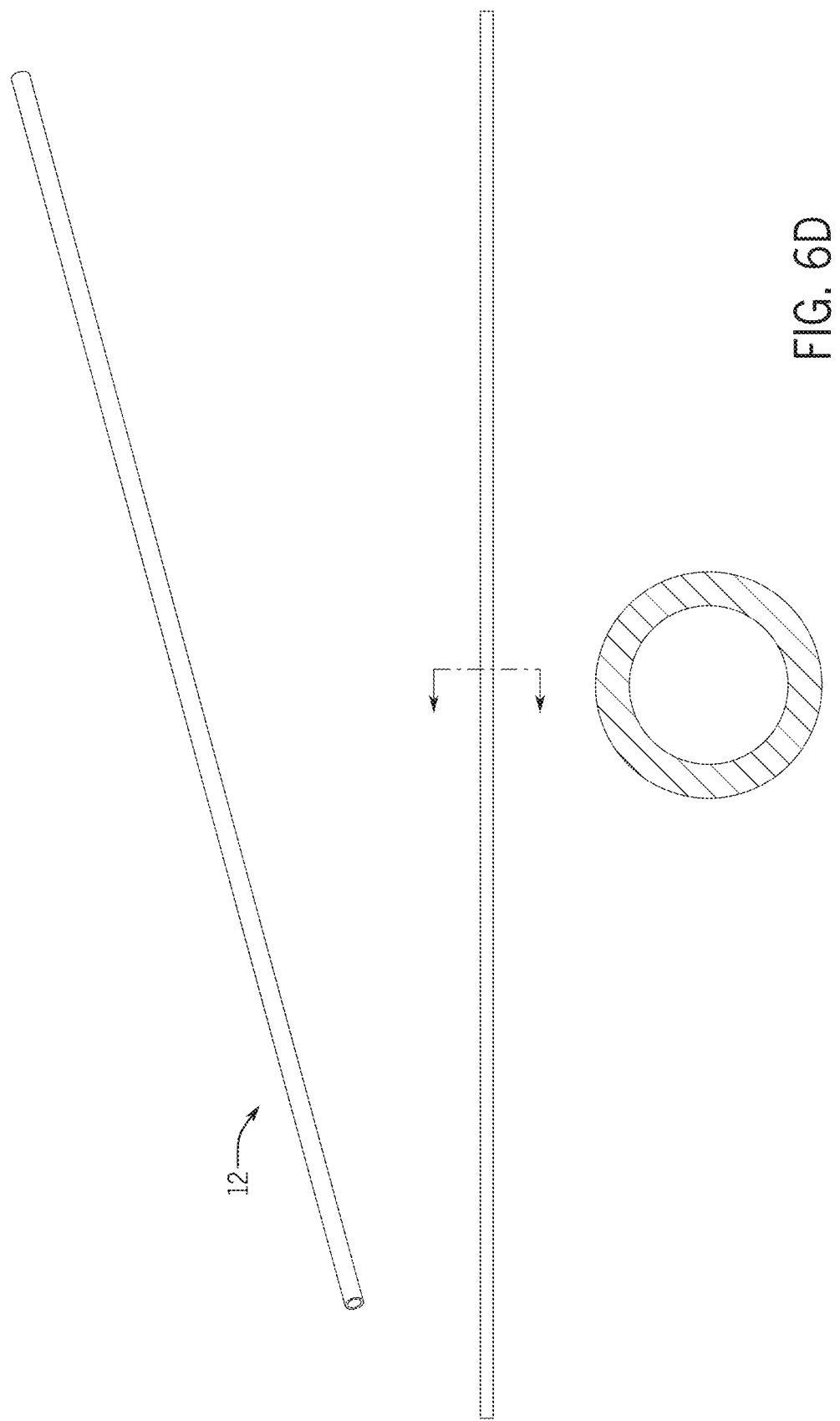
Figure 6E:
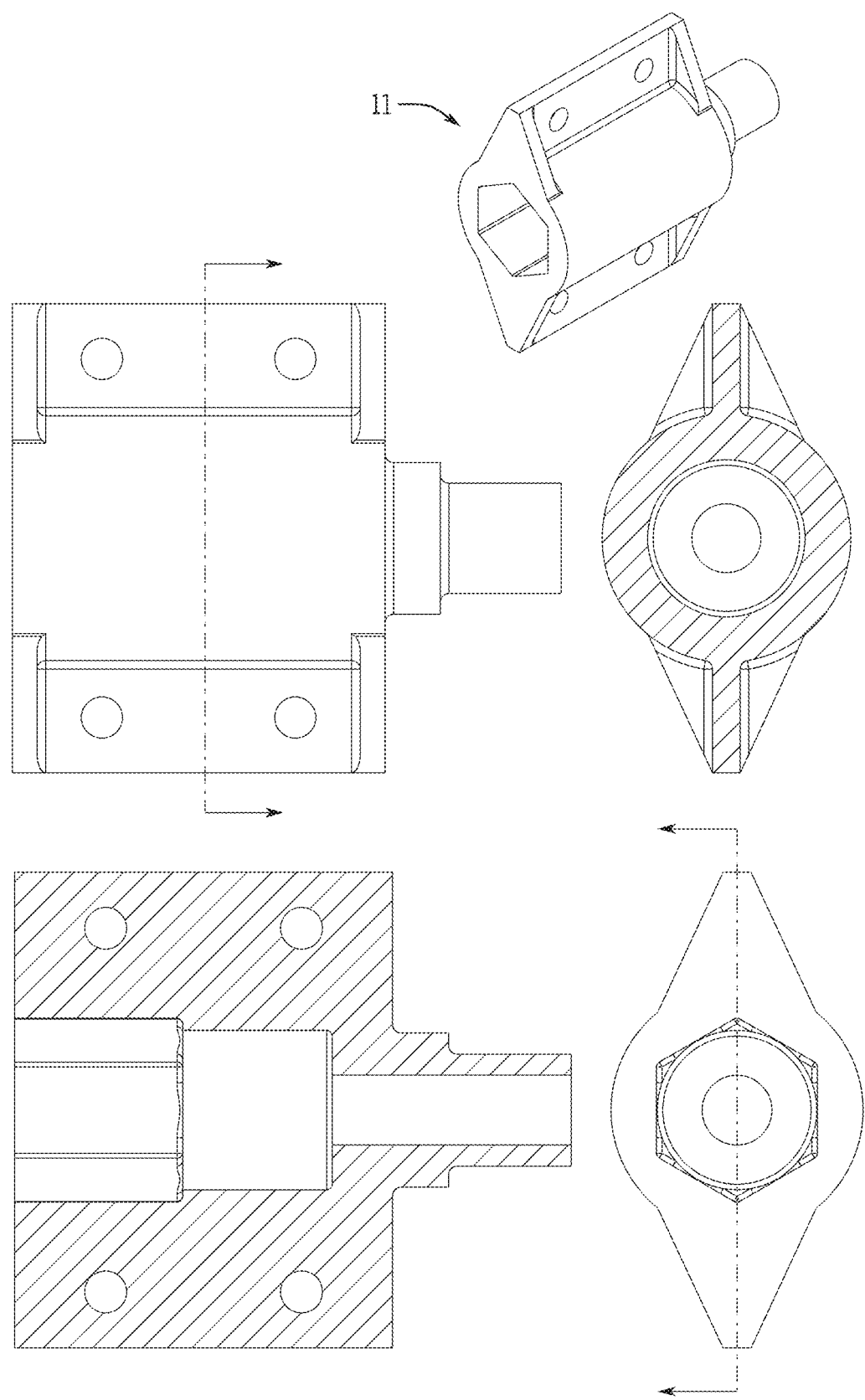
Figure 8:
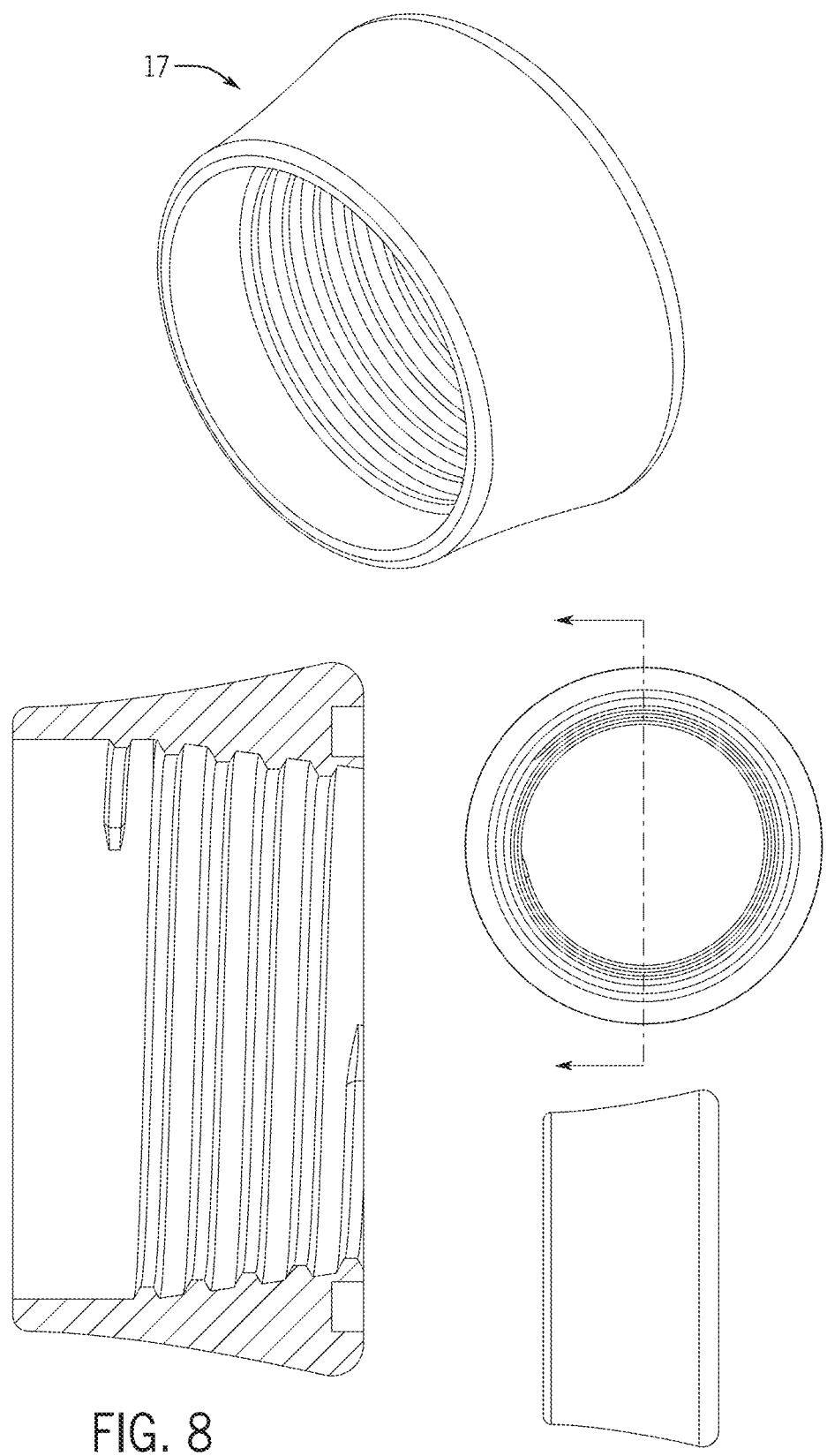
FIG. 8 shows a balljoint cap of an exemplary device of embodiments of the present disclosure.
Figure 9:
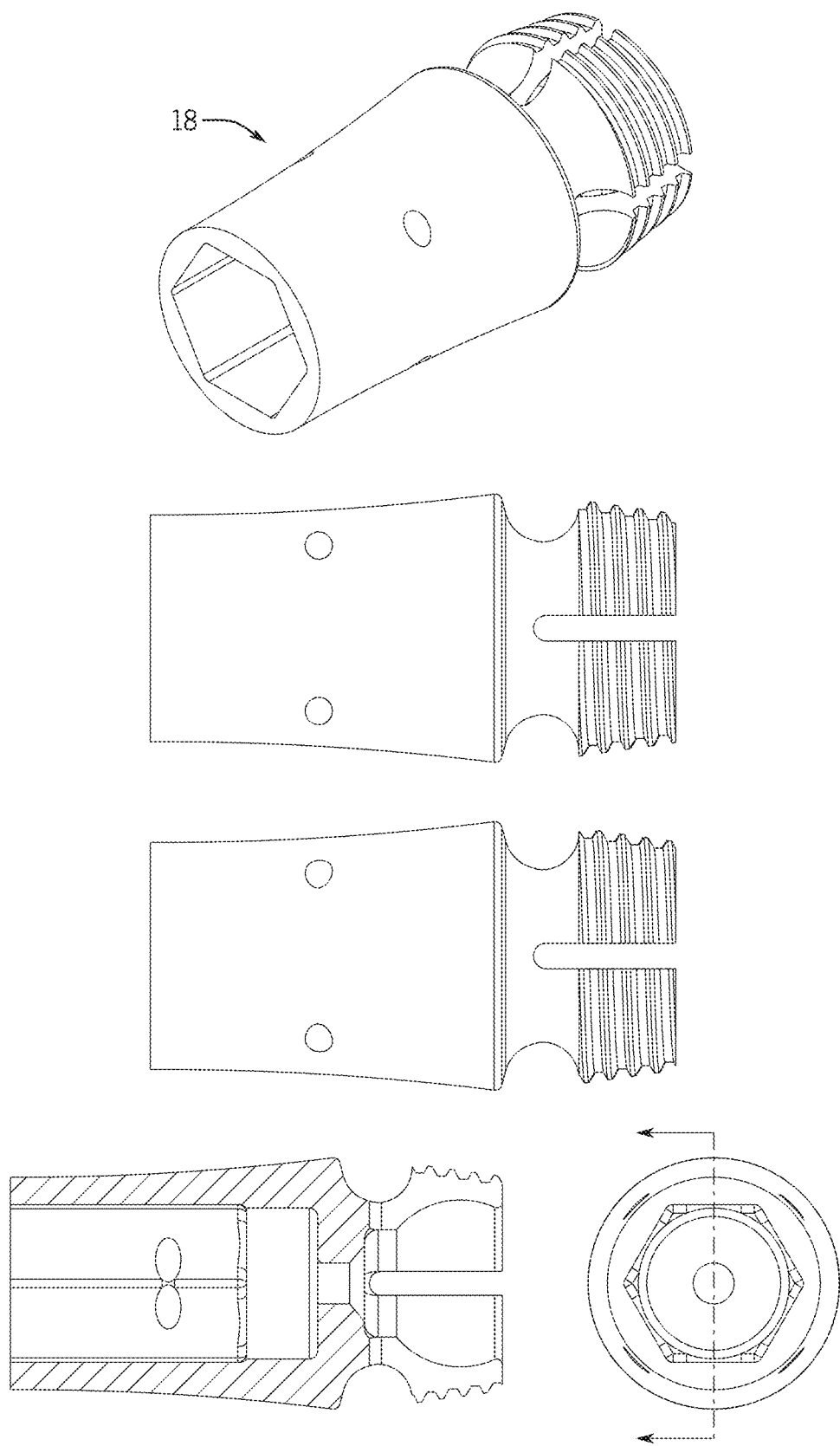
FIG. 9 shows a balljoint socket of an exemplary device of embodiments of the present disclosure.
Figure 13:
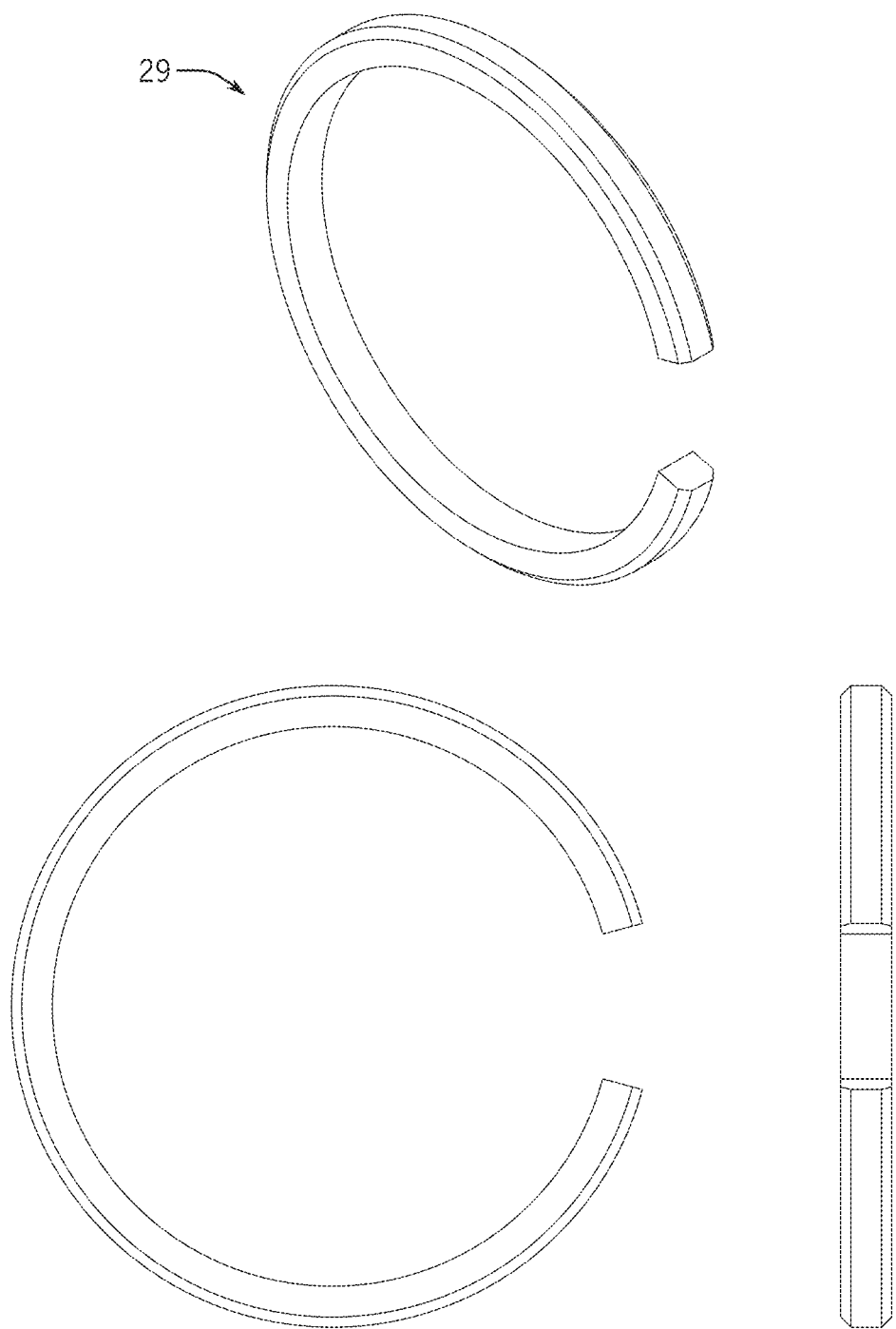
FIG. 13 shows a retainer ring of an exemplary device of embodiments of the present disclosure.

FIGS. 4, 5, 8, 12, and 13 show details of lamp 6. FIG. 4 shows details of the lamphead assembly. FIG. 4 shows lamphead aperture ring 24, lamphead lens retainer 23, lamphead lens 22, and lamphead screws 21. FIG. 5 shows further details of the lamphead assembly. FIG. 5 shows lamphead aperture ring 24, lamphead reflector 25, screw 26, lamphead PCB 27, lamphead ball joint body 28, and retainer 29. FIG. 5 further shows a line drawing and 3-dimensional rendering of assembled lamp 6. FIG. 8 shows a close up and dimensions of ball joint cap 17. FIG. 9 shows a close up and dimensions of balljoint socket 18. FIG. 12A shows a close up view of lamphead lens 22 and exemplary dimensions. FIG. 12B shows a close up view of lamphead lens retainer 23 and exemplary dimensions. FIG. 12C shows a close up view of lamphead lens ball joint 28 and exemplary dimensions. FIG. 12D shows a close up view of lamphead aperture ring 24 and exemplary dimensions. FIG. 12E shows a close up view of lamphead reflector 25 and exemplary dimensions. FIG. 13 shows a close up view of retainer 29 and exemplary dimensions.

The present disclosure is not limited to particular light source for use in light 1. In some embodiments, the light or lamp source comprises one or more light emitting diodes (LEDs), fluorescent, halogen, neon, incandescent, etc. In some embodiments, the light source emits light in the visible, ultraviolet, or infrared portions of the spectrum. In some embodiments, the light 1 comprises two or more different light sources that emit light of different wavelengths. In some embodiments, a switch or other activator is provided that permits a user to switch between different light options. For example, in some embodiments, a white light is used for a portion of a medical procedure and a second light (e.g., UV) is used for a second portion of a medical procedure to illuminate a contrast agent, dye, or other component contained in a patient tissue (e.g., to identify surgical margins; e.g., for assessing tumor boundaries). The switch may be contained on the lighting device or may be remote (e.g., a foot switch) that sends a signal (e.g., via wireless communication) to the light to switch configurations. In some embodiments, the light is configured to pulse. For example, in some embodiments, light of one wavelength is provided in a first pulse and light of a second wavelength is provided in a second pulse.

Figure 11:
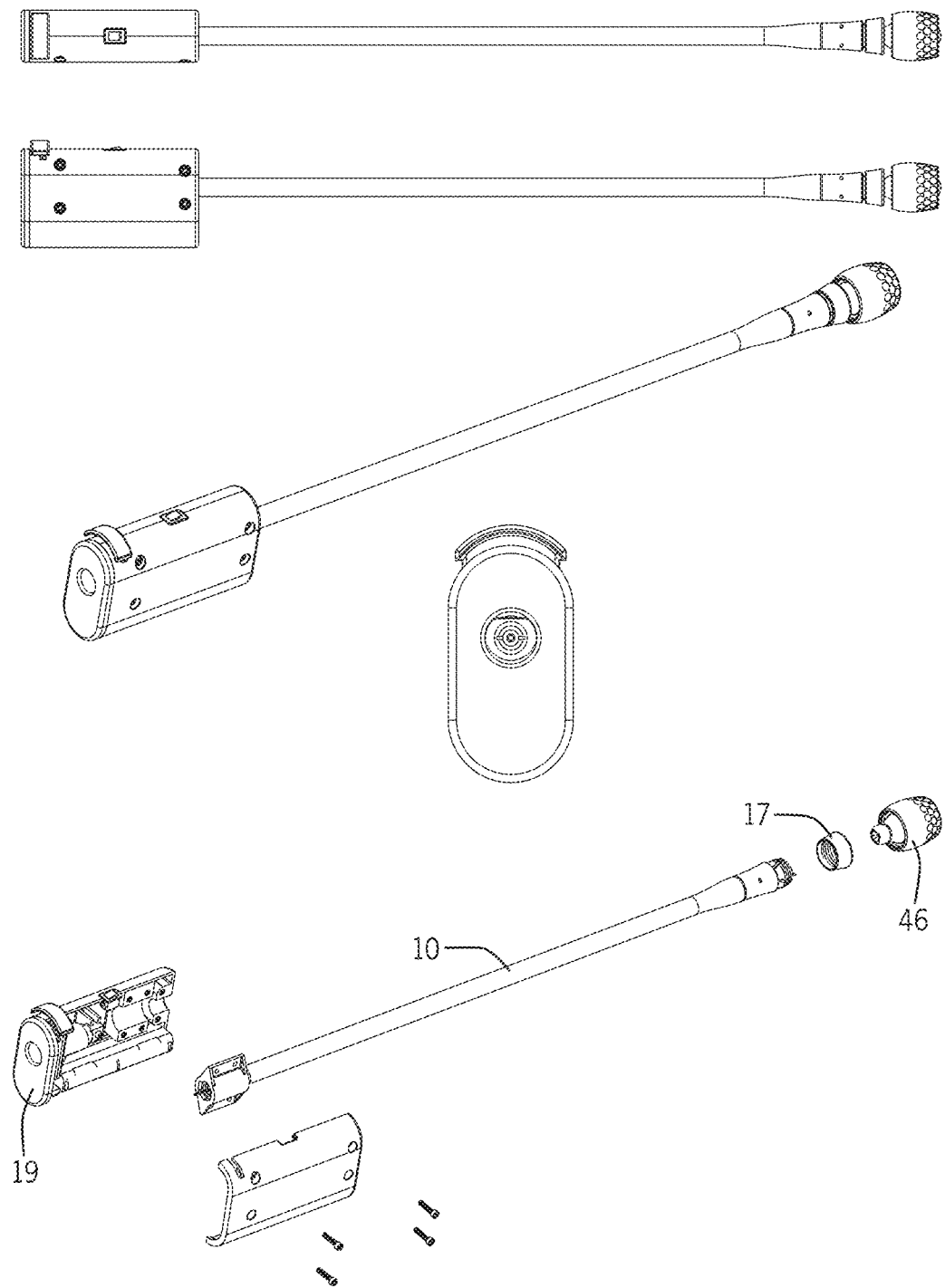
FIG. 11 shows an overview of the outside of a flexible arm with battery of an exemplary device of embodiments of the present disclosure.
Figure 12A:
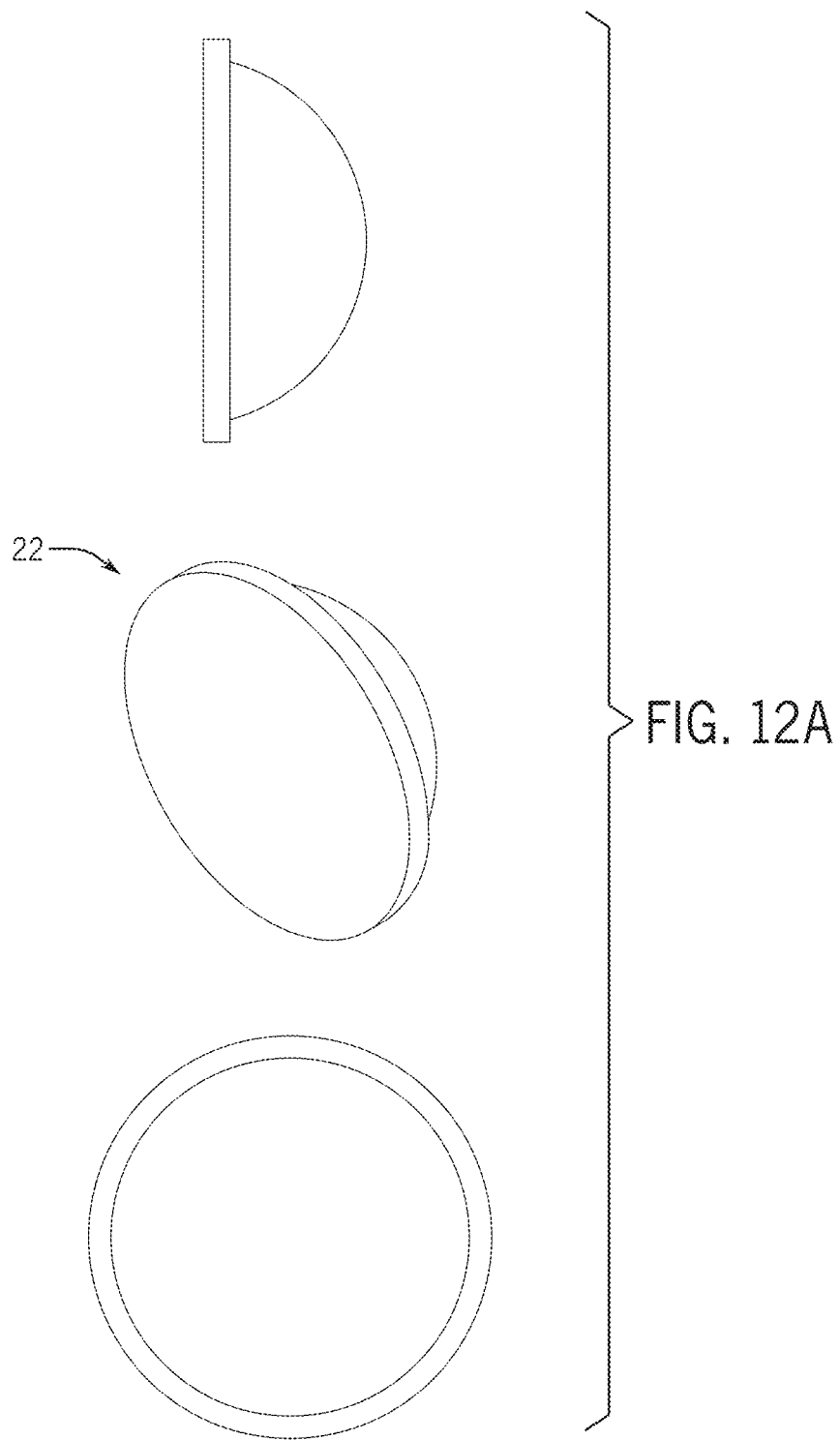
FIG. 12A-E shows a) a lens; b) a lens retainer; c) a lamphead balljoint body; d) an aperture ring; and e) lamphead reflector of an exemplary device of embodiments of the present disclosure.
Figure 12B:
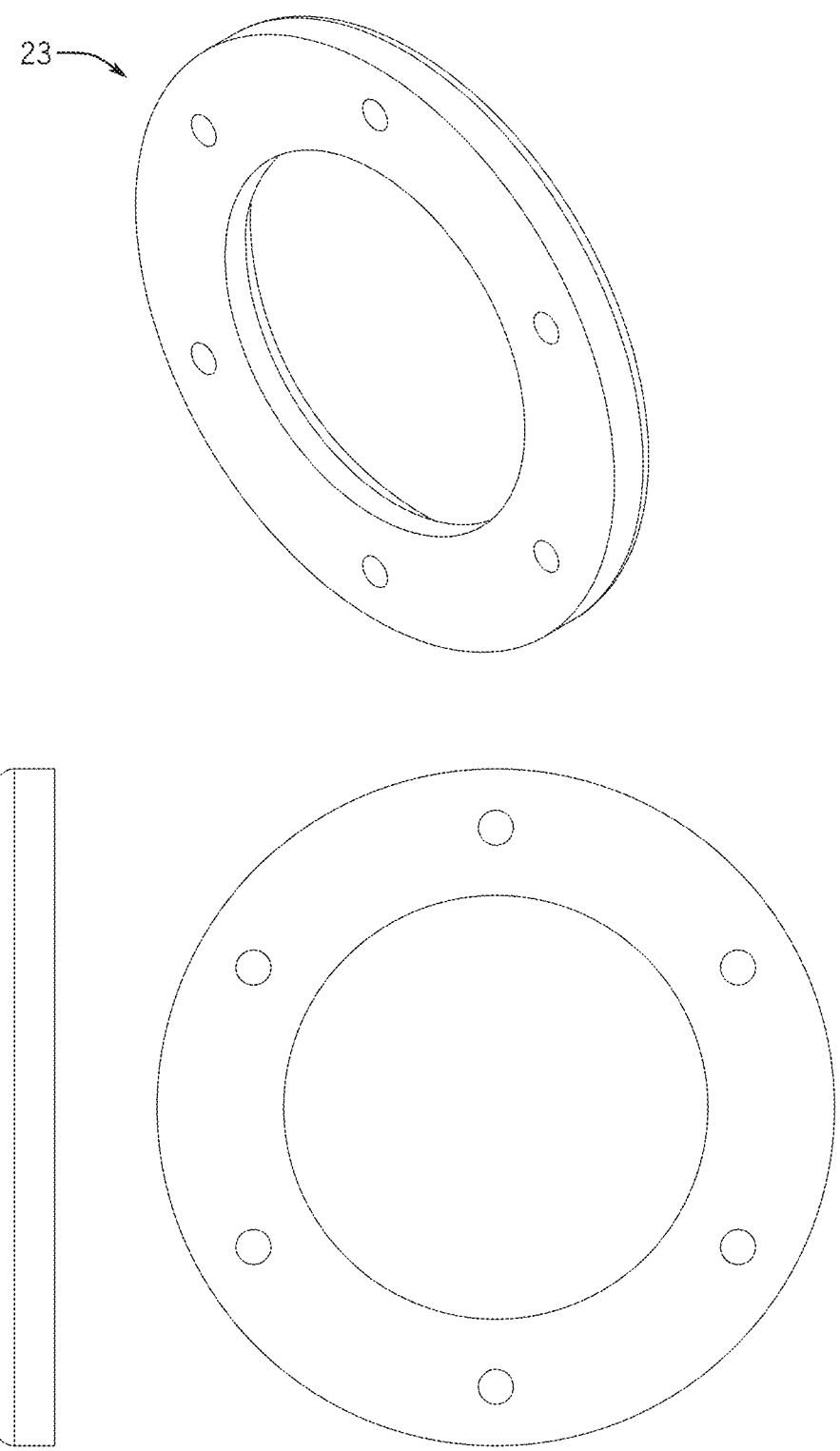
Figure 12C:
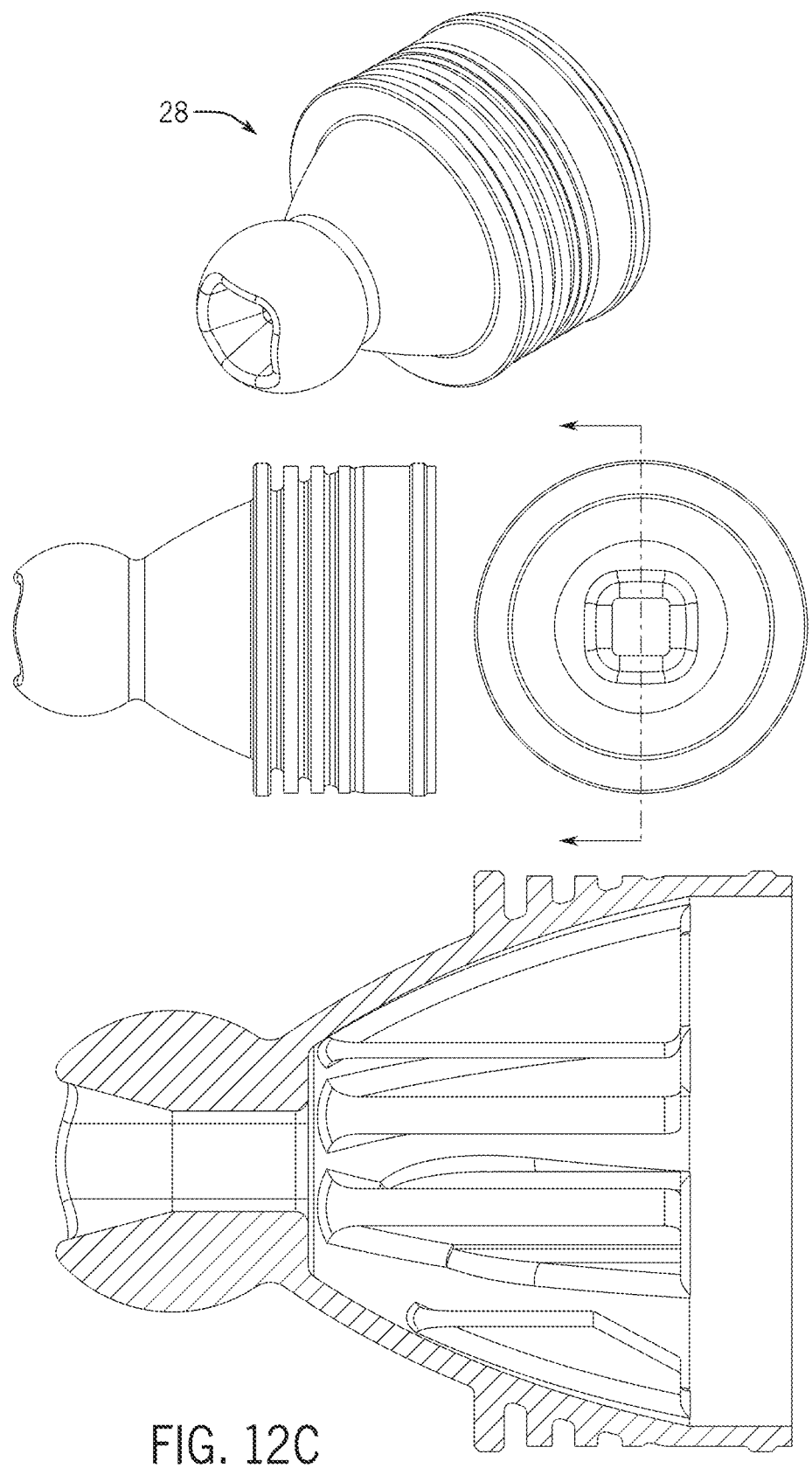
Figure 12D:
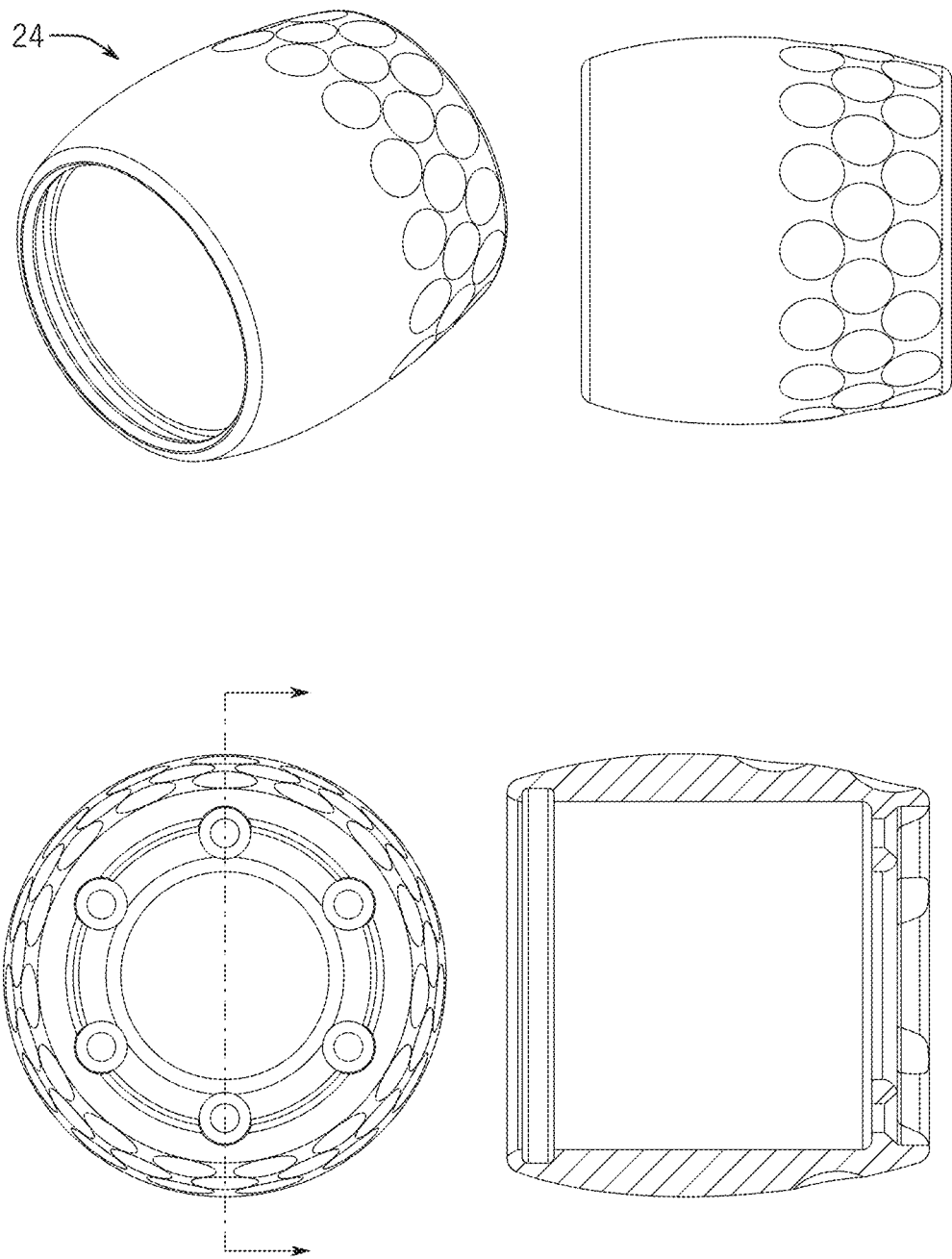
Figure 12E:
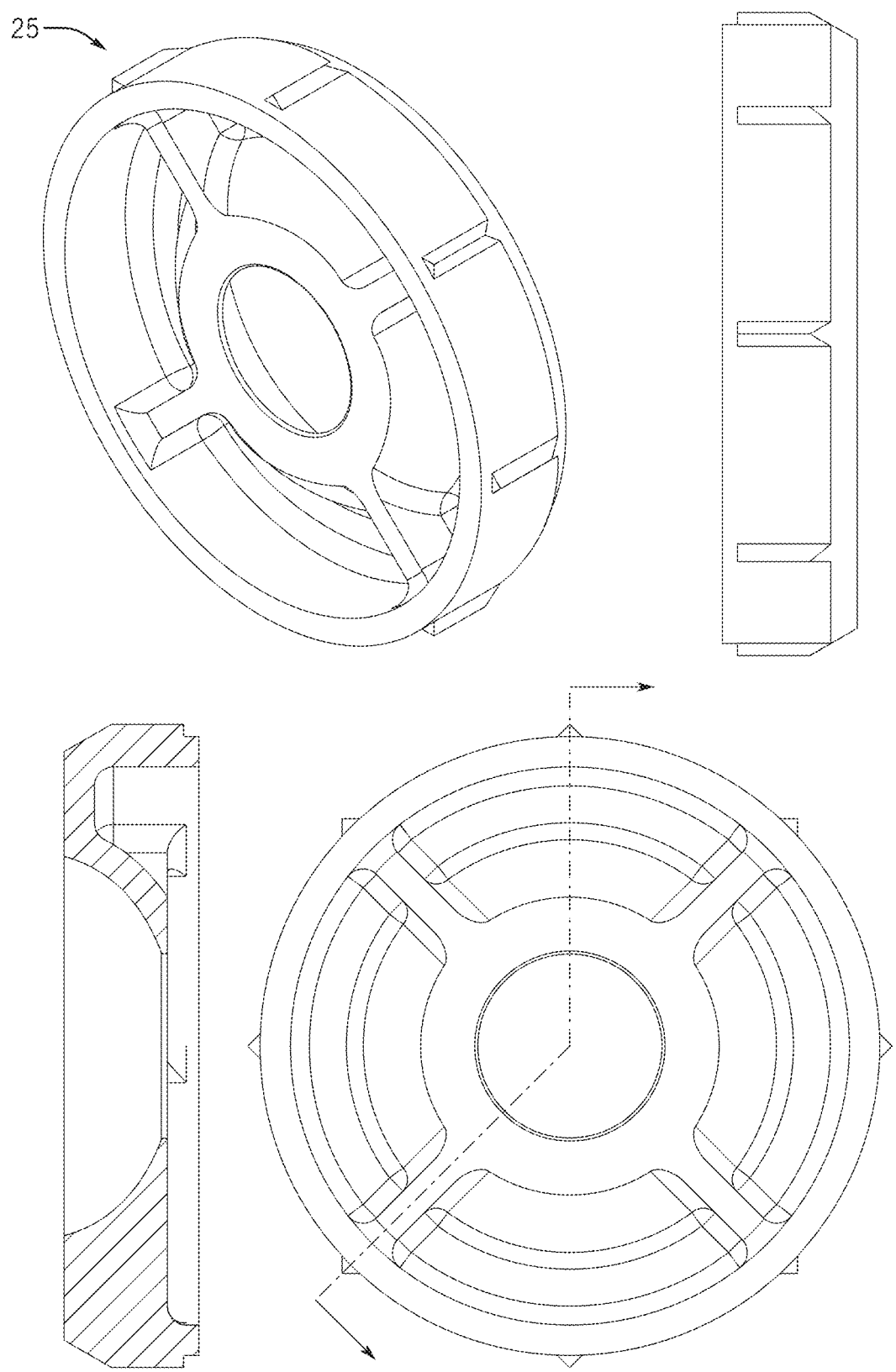

FIGS. 6 and 11 show a detail view of an exemplary flexible arm 10. Shown are flexible components 14 and rigid component 13. FIG. 6A further shows connector 35, battery housing 11, wire 33, connector 30, ball joint socket 15, and flexible arm screws 31. FIG. 6B shows a close up of the arm 10 showing battery housing 11 and ball joint socket 15. FIG. 6C shows a close up of tube 12. FIG. 6D shows a cross section and exemplary dimensions of tube 12. FIG. 6E shows a close up and exemplary dimensions of battery housing 11. FIG. 11 shows a close and dimensions of aspects of flexible arm 10. Shown are battery housing support end 19, ball joint cap 17, and lamphead assembly 46.

In some embodiments, the lengths of the flexible sections and the rigid section are present at a ratio of 1:2 to 2:1 or any values therein between (e.g., 1:1.9, 1:1.8, 1:1.7, 1:1.6, 1:1.5, 1:1.4, 1:1.3, 1:1.2, 1:1.1, 1:1, 1.1:1, 1.2:1, 1.3:1, 1.4:1, 1.5:1, 1.6:1, 1.7:1, 1.8:1, 1.9:1), although other ratios are specifically contemplated. In some embodiments, the length of the entire light including flexible and rigid components and power supply is 10-40 inches in length (e.g., 10, 15, 20, 25, 30, 35, or 40 inches or a fraction thereof). In some embodiments, the rigid component is 1-10 inches in length (e.g., 1, 2, 3, 4, 5, 6, 7, 8, 9, or 10 inches or a fraction thereof). In some embodiments, the flexible component(s) is 1-15 inches in length (e.g., 1, 2, 3, 4, 5, 6, 7, 8, 9, 10, 11, 12, 13, 14, or 15 inches or a fraction thereof).

In some embodiments, the flexible arm comprises power connector 11 configured for connection to a power component (e.g., battery pack) and lamp connector 15 configured for attached to a lamp component. In some embodiments, the flexible arm comprises a tube 12 that contains the rigid and flexible components.

Figure 7:
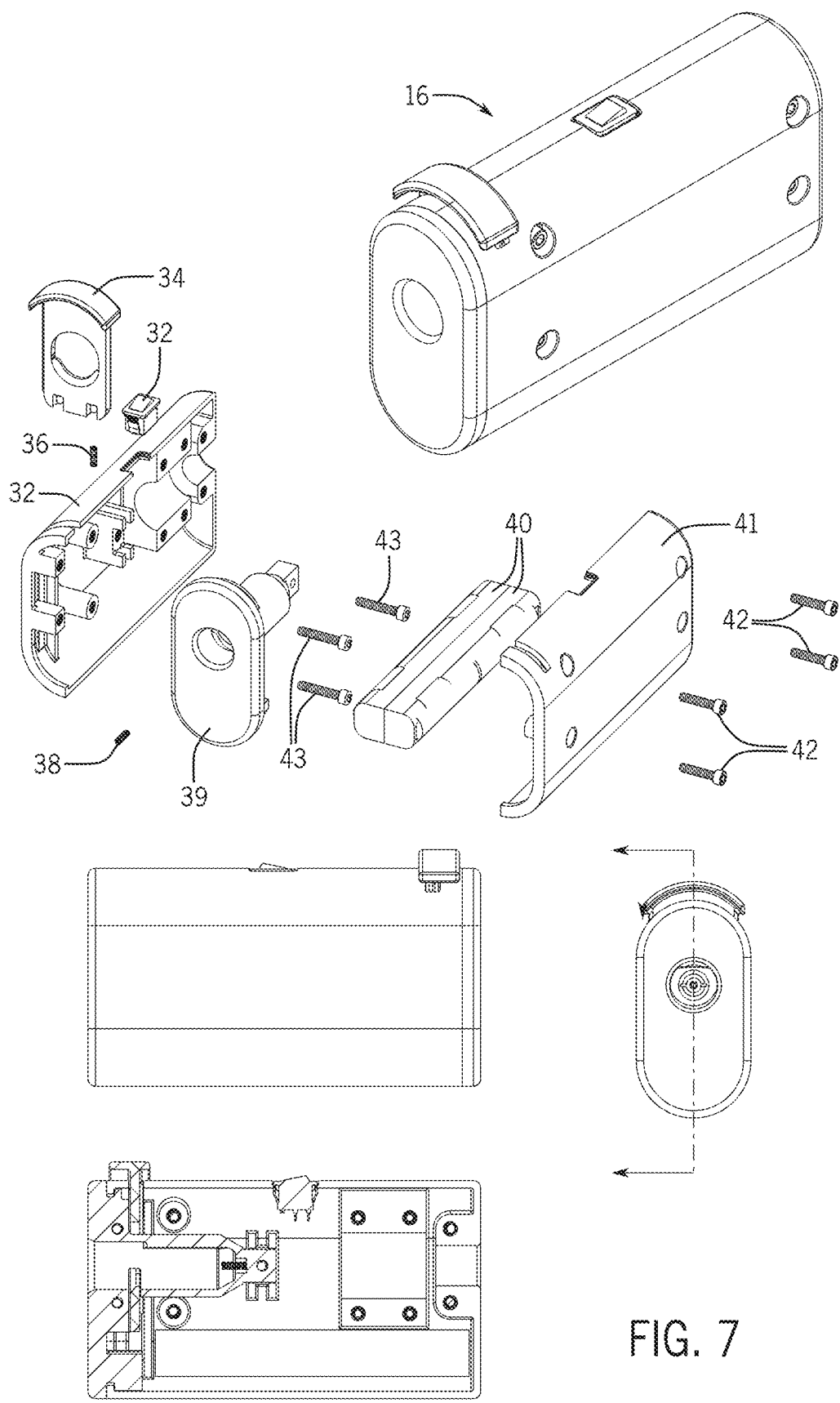
FIG. 7 shows an overview of a battery component of an exemplary device of embodiments of the present disclosure.
Figure 10A:
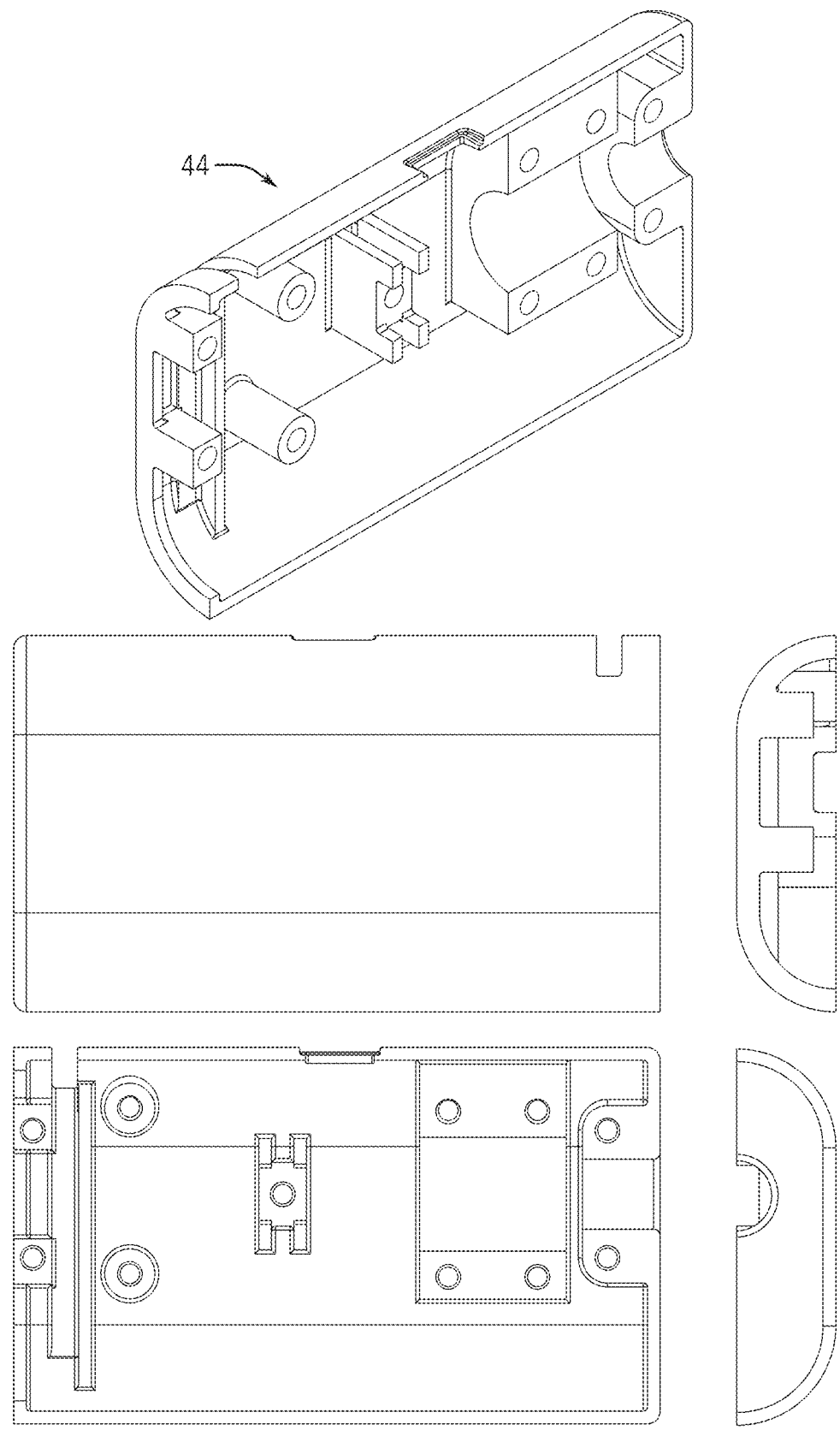
FIG. 10A-C shows a) a left side view of a battery component; b) a right side view of a battery component; and c) a battery support of an exemplary device of embodiments of the present disclosure.
Figure 10B:
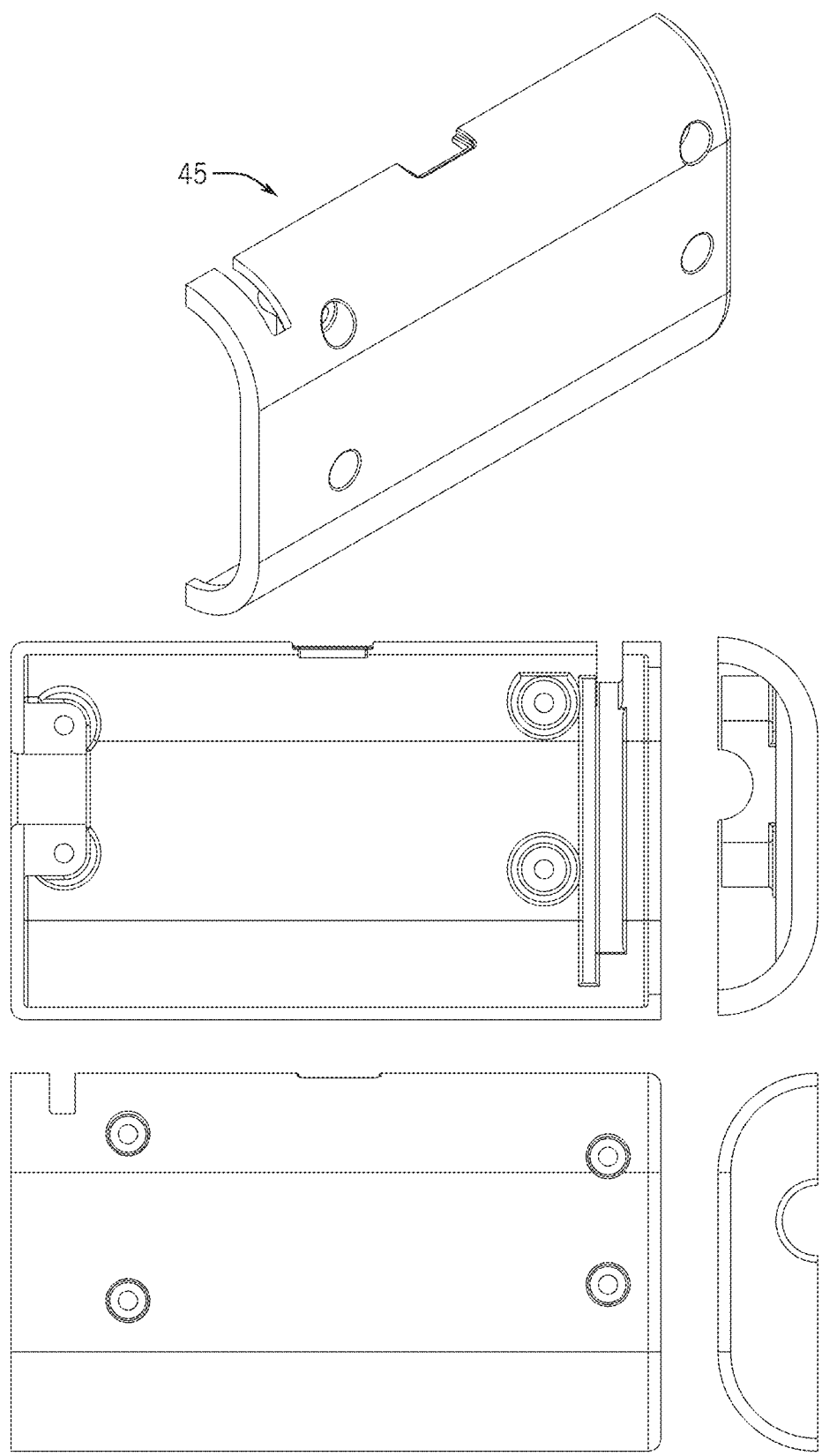
Figure 10C:
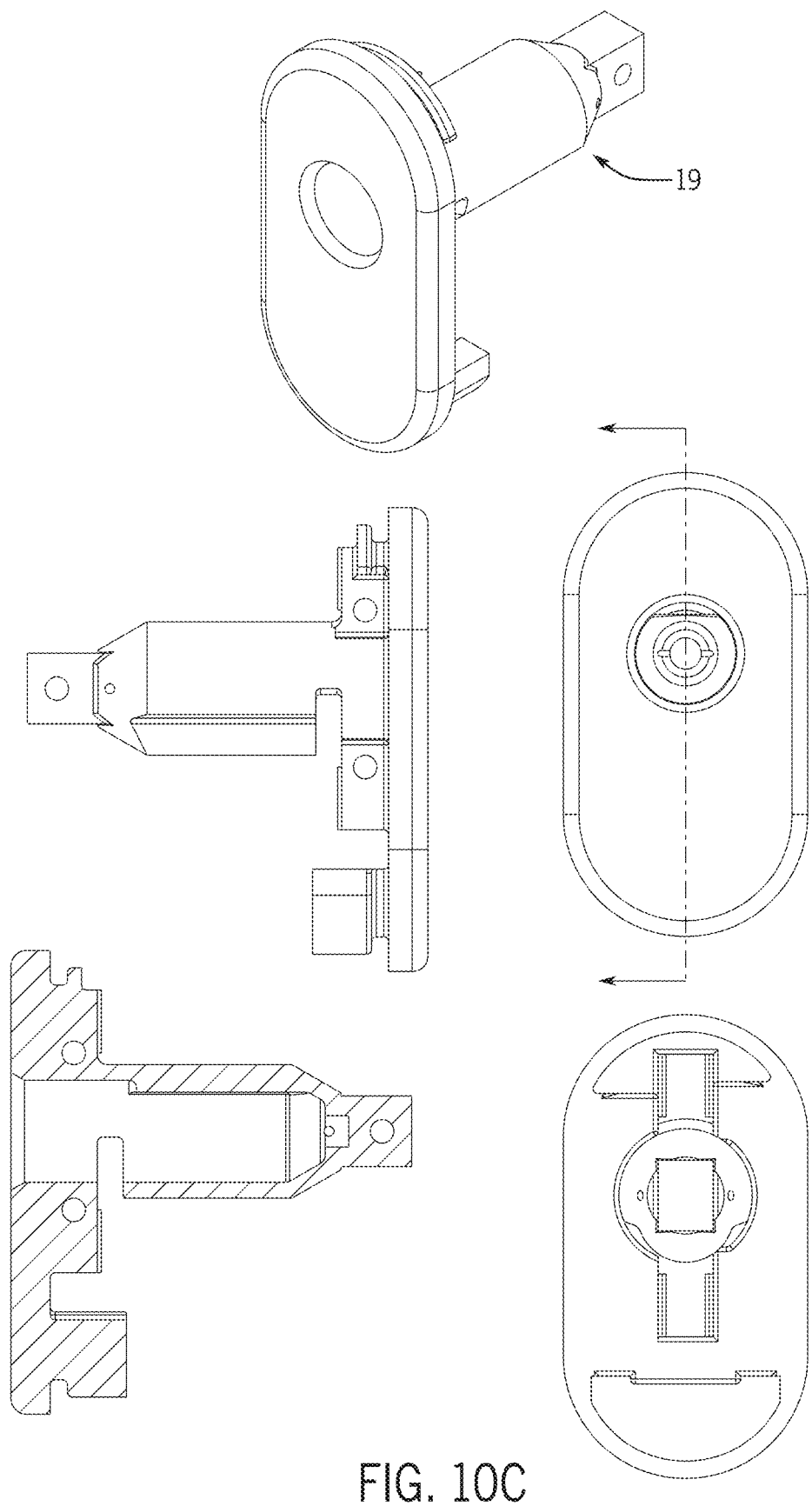
Figure 14:
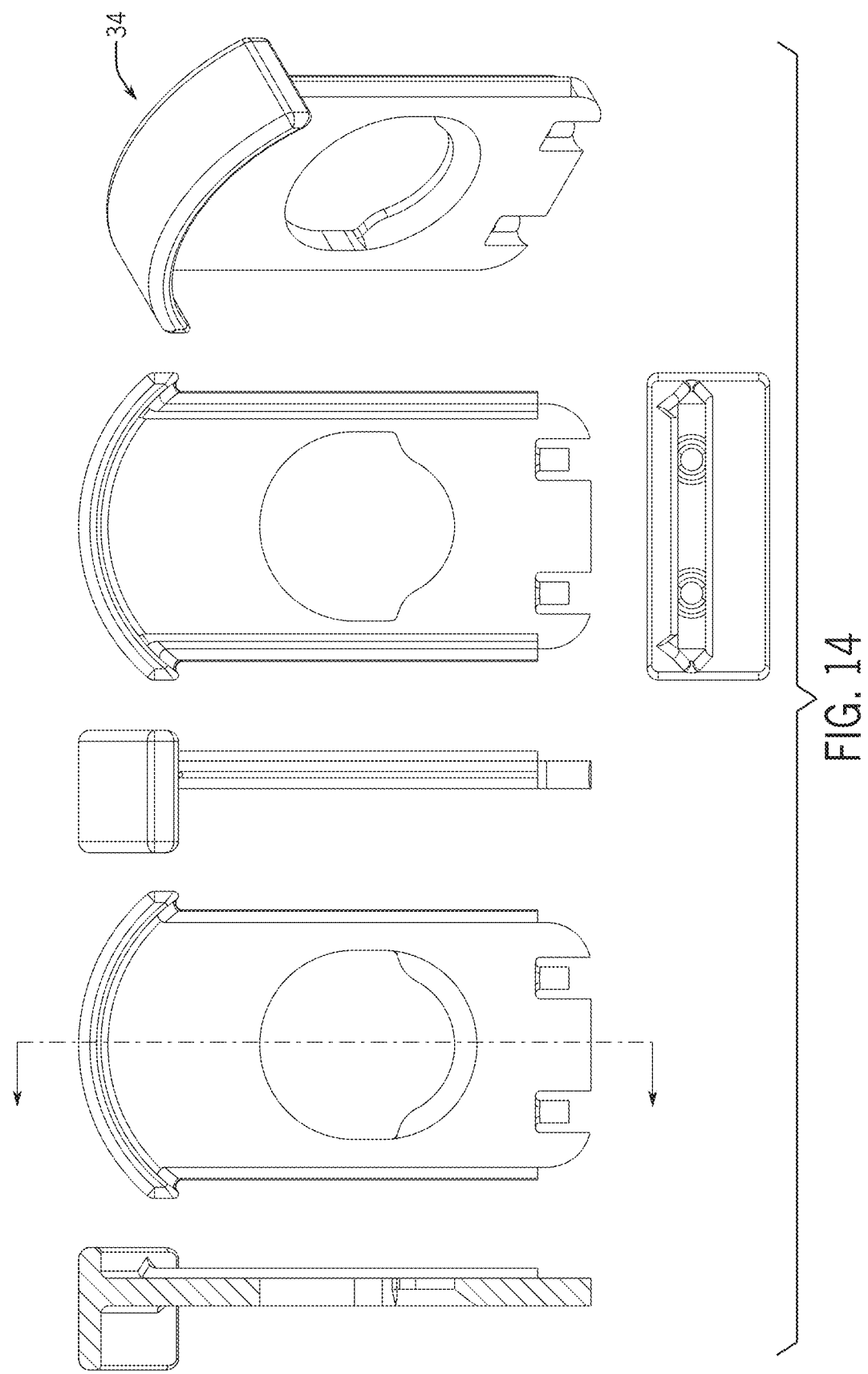
FIG. 14 shows a side lock of an exemplary device of embodiments of the present disclosure.

FIGS. 7, 10, and 14 show a detail view of an exemplary power supply (e.g., battery pack) 16. FIG. 7 shows left battery housing 37, right battery housing 41, battery housing support end 39, slide lock 34, cartridge spring 38, screws 42 and 43, battery 40, and digital key 32. FIGS. 10A and 10B show close ups and dimensions of left battery housing 44 and right battery housing 45. FIG. 19C shows a close up and dimensions of battery housing support end 19. FIG. 14 shows a close up view of slide lock 34 and exemplary dimensions. In some embodiments, slide lock 34 is replaced with a twisting bayonet lock (not shown).

Figure 15:
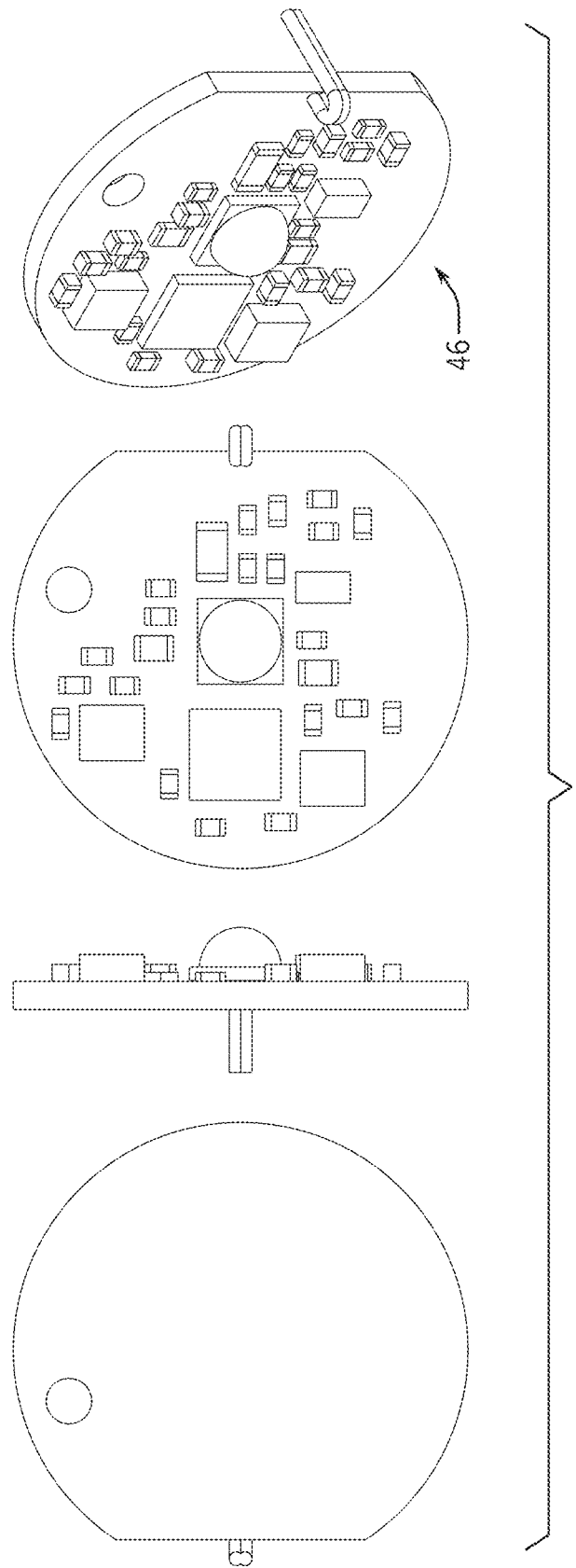
FIG. 15 shows a SMT of an exemplary device of embodiments of the present disclosure.

FIG. 15 shows a close up view of PCB board 46 and exemplary dimensions. Table 1 below shows exemplary sizes and sources for components of the device and system.

TABLE 1

| PART | Description | Process | Part Material | Part Size (In) | Part Volume (In^3) | Wall Thickness (In) | Projected Area(In^2) | Part Weight (LBS) |
|---|---|---|---|---|---|---|---|---|
| Top Level Assembly | | Assembly | | | | | | |
| Battery Hsg Asm | | Assembly | | | | | | |
| Cpt-A Battery Hsg Left | | Injection Molded | ABS-Black | 5.075 × 2.955 × 0.778 | 3.64 | 0.1 | 14.996 | 0.13 |
| Cpt-A Battery Hsg Right | | Injection Molded | ABS-Black | 5.075 × 2.955 × 0.778 | 2.5367 | 0.1 | 14.996 | 0.0935 |
| Cpt-A Battery Hsg SupportEnd | | Injection Molded | ABS-Black | 2.550 × 2.955 × 1.555 | 1.7234 | 0.25 | 40% | 0.0623 |
| Cpt-A Slide Lock | | Injection Molded | Acetyl-Black | 2.300 × 1.380 × .550 | 0.31 | 0.125 | 90 | 0.011 |
| 99362A300 | McMaster-Insert-Screw in #6-32 | | | | | | | |
| Spring, Carriage, CSC 10007 | | Std Part | | | | | | |
| 92196A150 | McMaster-Screw #6-32-SHCS X 0.75 | Std Part | 410 Stainless Steel | | | | | |
| 92196A151 | McMaster-Screw #6-32-SHCS X 0.625 | Std Part | 410 Stainless Steel | | | | | |
| InLine AA Battery Asm | | Assembly | | | | | | |
| McM 7712K15 AA InLine BatteryHolder | McMaster-Battery Holder | | | | | | | |
| AA Battery | Battery | Std Part | | | | | | |
| DigKey-CH865-ND | Digikey Switch | Std Part | | | | | | |
| Cpt-A FlexArm Center OM | | OverMold | Santoprene 201-80-Black | 22.48 × 1.7 × .92 | 4.2197 | 0.24 | 10.726 | 0.1495 |
| Cpt-A FlexArm Asm Insert | | Assembly | | | | | | |
| Cpt-A FlexArm End BatteryHsg | | Injection Molded | ABS-Black | 1.988 × 17 × .9 | 0.07468 | 0.162 | 2.58 | 0.0275 |
| Cpt-A Flexarm-Tube | Mc Master-5177K62-3/16 Aluminum Tubing | | Aluminum | | | | | |
| 50915K214 | Mc Master-Tube Fitting 3/16 to 1/8NPT | | | | | | | |

TABLE 1-continued

| PART | Description | Process | Part Material | Part Size (In) | Part Volume (In^3) | Wall Thickness (In) | Projected Area(In^2) | Part Weight (LBS) |
|---|---|---|---|---|---|---|---|---|
| Cpt-A BallJoint Socket | | Injection Molded | | 179 × .92 × .92 | 0.445 | 0.18 | 1.48 | 0.0164 |
| 97395A433 | McMaster Dowel Pin-3/32Dia x 0.75 | | | | | | | |
| Cpt-A Flexarm-Support | McMaster-5176K23 - 1/4 in steel tubing | Std Part | | | | | | |
| Cpt-A FlexArm 2-Wire | Red and Black 22 gauge wire c 30 inches | Std Part | | | | | | |
| LampHead Asm | | Assembly | | | | | | |
| Cpt-A LampHead BallJoint Body | | Die Cast | Aluminum | 1.12 × 1.12 × 1.41 | 0.3441 | 0.05 | 0.9852 | 0.0336 |
| Light Head Aperture SubAsm | | Assembly | | | | | | |
| Cpt-A LampHead Aperture Ring | | Injection Molded | ABS-White | 1.47 × 1.47 × 1.41 | 0.711 | 0.157 | 1.7 | 0.0259 |
| Cpt-A LampHead Lens Retainer | | Die cast | Aluminum | 1.15 × 1.15 × .1 | 0.0556 | 0.1 | 1.039 | 0.0054 |
| Cpt-A LampHead Lens | Henglilens-HL-19.8T | Standard Part | Lexan | | | | | |
| 92210A017 | McMaster #1-72 FHCS X0.1875 | Std Part | Stainless Steel | | | | | |
| Cpt-A LampHead Reflector | | Injection Molded | ABS-HiTemp | 1.06 × 1.06 × .222 | 0.0705 | 0.05 | 0.817 | 0.00261 |
| SMT 1 Inch PCB-0556-00 | | Assembly | SMT | | | | | |
| 90272A077 | McMaster #2-56 X 0.25 18-8 Stainless | Std Part | 18-8 Stainless | | | | | |
| Cpt-A Retainer | | Injection Molded | ABS-Black | 1.25 × 1.25 × .1 | 0.026 | 0.1 | 0.2695 | 0.001 |
| Cpt-A BallJoint Cap | | Injection Molded | ABS-Black | 1.12 × 1.12 × 0.550 | 0.1609 | 0.179 | 0.9852 | 0.0059 |

Figure 16:
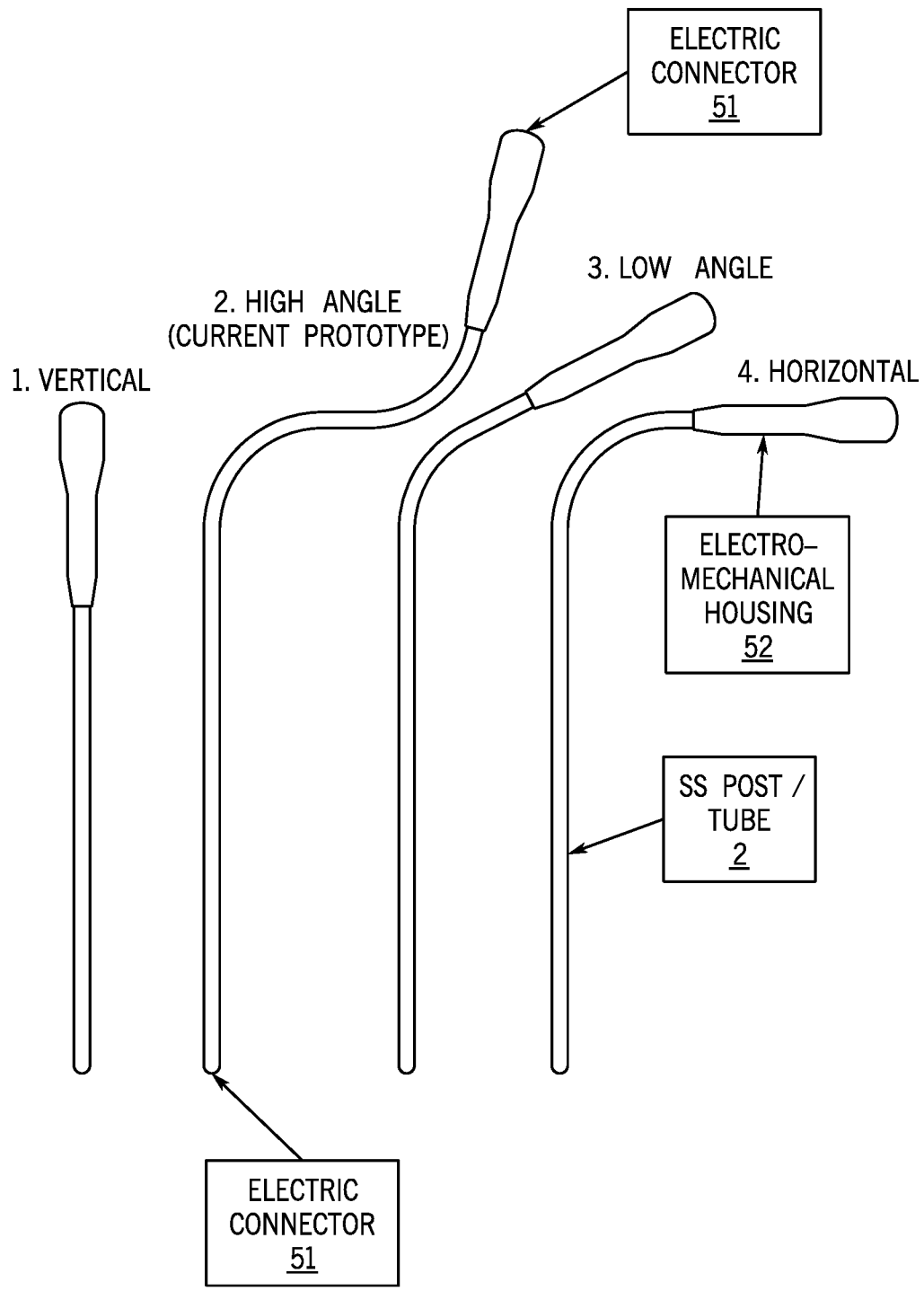
FIG. 16 shows exemplary arm configurations of devices of embodiments of the present disclosure.

FIGS. 16-19 show additional features of the light. FIG. 16 shows solid support 2 in a variety of different angle configuration. For example, the left view shows solid support 2 in a vertical orientation with light 1 (not shown) pointing vertically. The second from the left view shows a high angle configuration where the solid support comprises an S-shaped curve with the light 1 (not shown) pointing at a high angle relative to the horizontal plane. The second from the right view shows solid support 2 at a low angle with a single bend and the light 1 (not shown) pointing at a low horizontal angle. The right view shows solid support 2 at horizontal angle with light 1 (not shown) pointing horizontally.

Still referring to FIG. 16, additional components of the light system are shown. For example, shown are electrical connectors 51 and electro-mechanical housing 52. The design of the electric connector 51 at either end of the post is easily modified to add pin outs for different functions without affecting the other parts of the system. The electro-mechanical housing 52 can be attached to different geometries and configurations of the solid support 2 to address different use cases or surgeon preferences, while still allowing the base of the light to be at or near the centerline of the medical procedure table. The design of the electric connector 51 at either or both ends of the solid support can be easily modified to add pin outs for different functions without affecting the other parts of the system. This is suitable for a variety of different purposes including, but not limited to, lighting, imaging, monitoring, etc.

Figure 17:
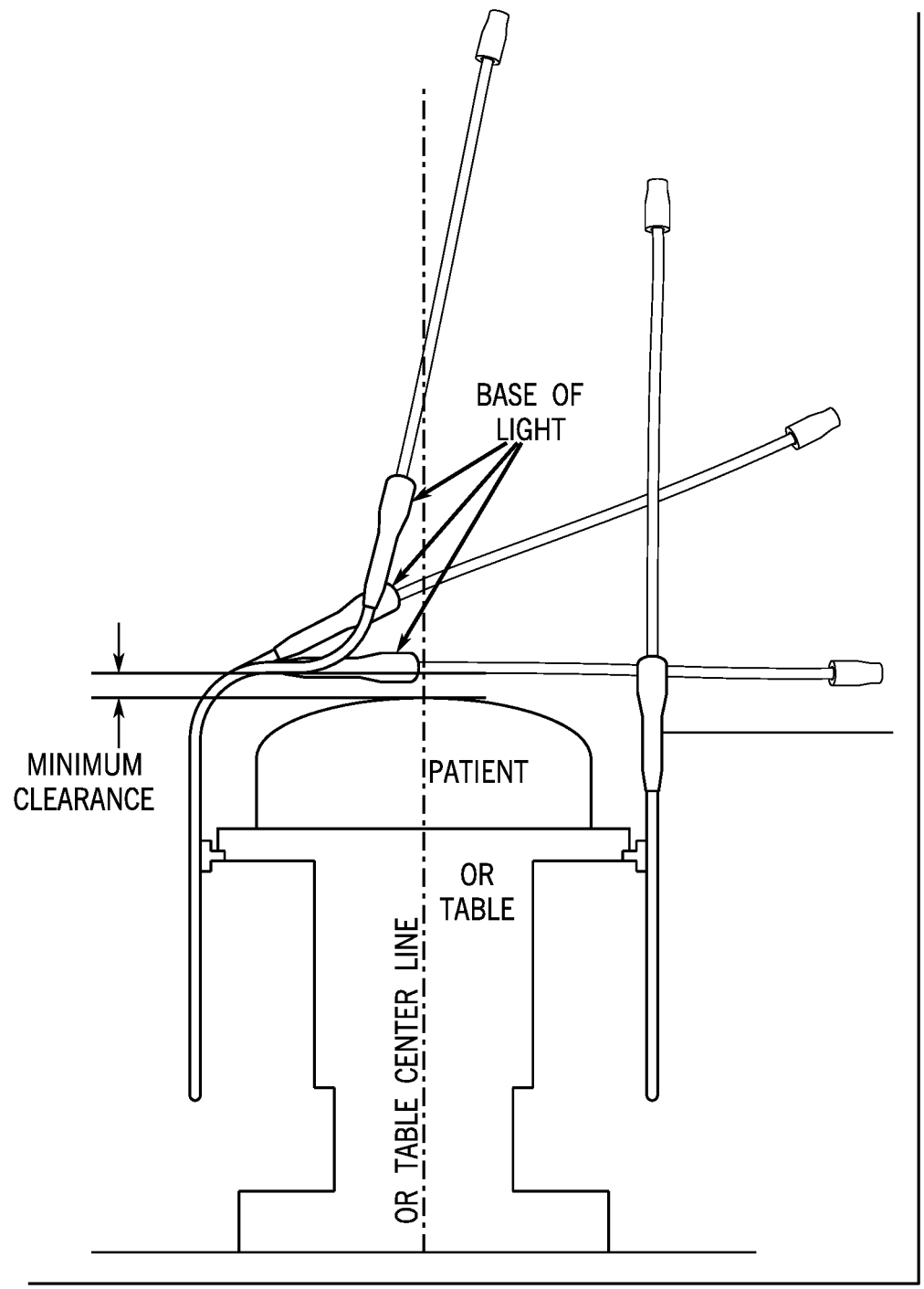
FIG. 17 shows an exemplary device of embodiments of the present disclosure positioned over an operating room table.

FIG. 17 shows the light 1 centered over a medical procedure (e.g., OR) table or surface. In some embodiments, the light 1 is positioned directly over or near the centerline of the medical procedure table. As shown in FIG. 17, a minimum clearance is provided between the solid support 2 and the patient on the medical procedure. In some embodiments, as shown in FIG. 17, multiple lights are utilized with a single medical procedure table. As described in FIG. 16 and illustrated in FIG. 17, the light 1 can be placed at a variety of different angle relative to the patient.

Figure 18A:
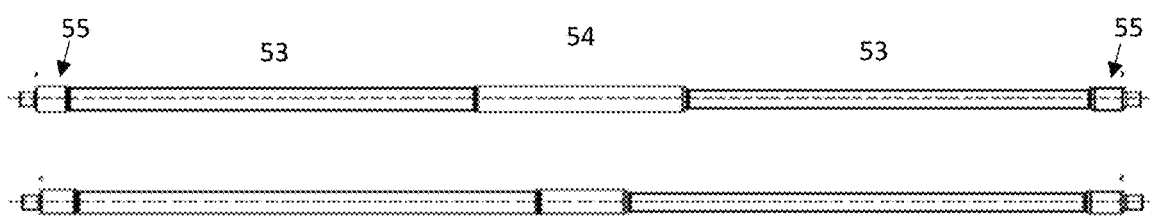
FIG. 18A-C shows exemplary sections of a flexible arm of a device of embodiments of the present disclosure.
Figure 18B:
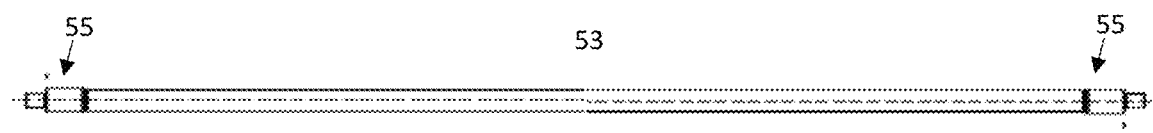
Figure 18C:
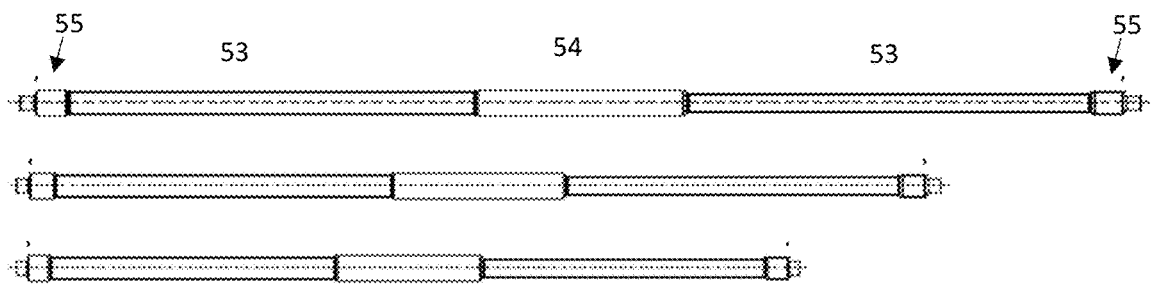

FIG. 18A-C shows different configurations of the flexible arm 10. The flexible arm 10 can be changed in length, diameter and material type without retooling. The proportion of rigid to flexible sections of the flexible arm can be varied as described in more detail below.

FIG. 18A shows configurations of flexible arm 10 with different proportions of rigid section(s) 54 and flexible section(s) 53. In FIG. 18A, a single rigid section 54 is centered between two equal length flexible sections 53. The top view shows an embodiment with a longer rigid section 54 and the bottom view shows an embodiment with smaller rigid section 54.

FIG. 18B shows an embodiment of a flexible arm 10 without a rigid section. The entire flexible arm portion of flexible arm 10 is flexible.

FIG. 18C shows further embodiments with different proportions of rigid sections 54 to flexible sections 53. In FIG. 18C, a single rigid section 54 is located between two flexible sections 53. The three views show different lengths of rigid 54 and flexible 53 sections.

FIGS. 18A-C further shows threaded ferrules 55. In FIG. 18, the threaded ferrules 55 are located on each end of the flexible arm 10 allow for the attachment of different functional modules (e.g., during or after manufacture). The threaded ferrules 55 further allow for disassembly at the end of life of the light 1.

Figure 19A:
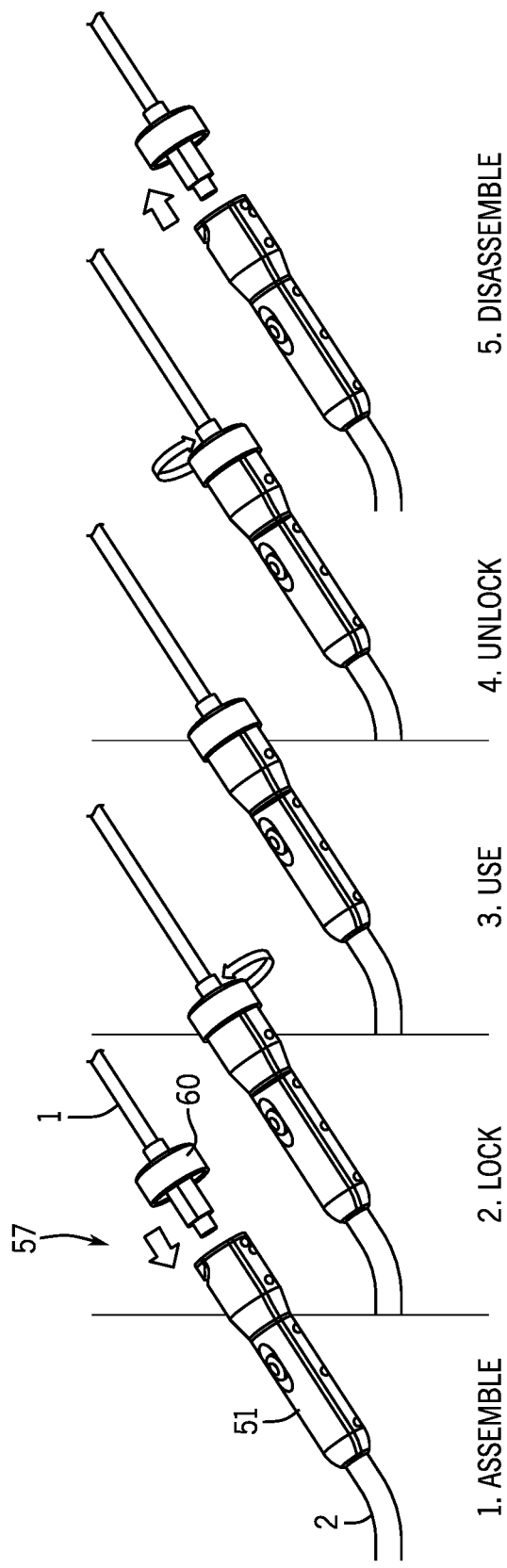
FIG. 19A-B show modularity and connections of exemplary devices of embodiments of the present disclosure.
Figure 19B:
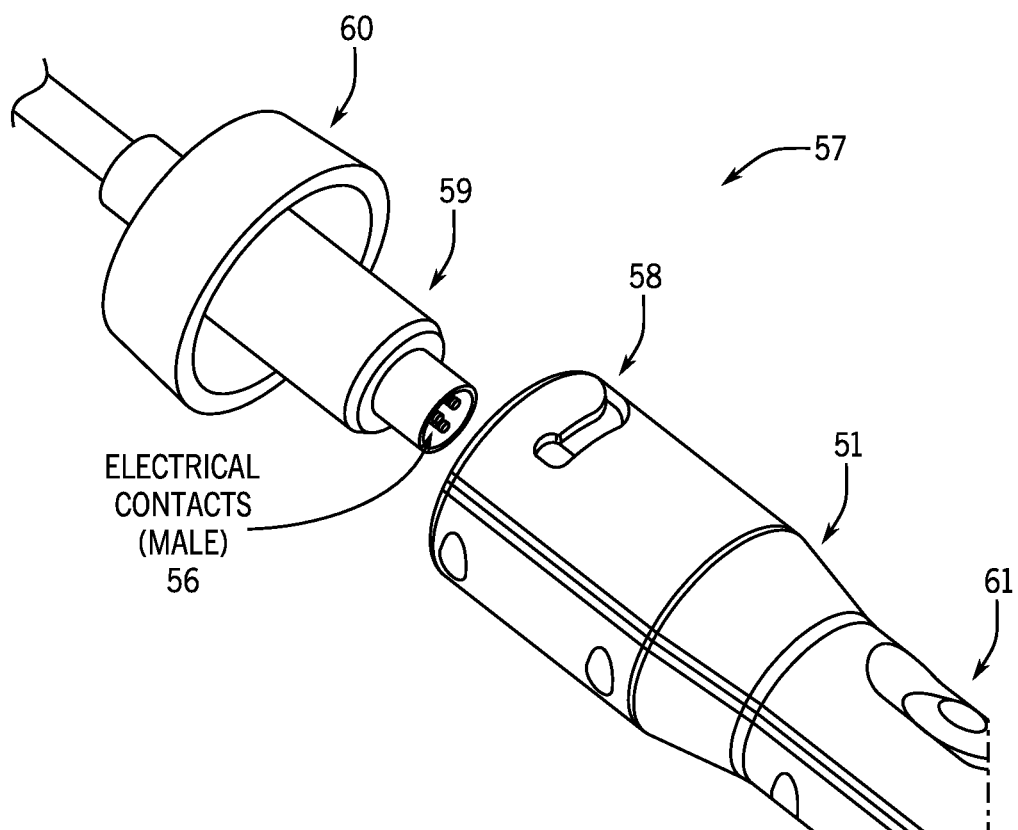

FIGS. 19A-B shows details of an exemplary connector component 57 that attaches the light 1 comprising flexible arm 10 to solid support 2. In the shown embodiments, no fasteners or tools are needed for attachment and disassembly of the light. The connector component 57 allows for rapid assembly and disassembly, and provides a safe electrical connection that is rigid and durable. The sealed design allows for manual wipe down (decontamination) and autoclaving (sterilization). In some embodiments, the connector component 57 includes an indicator light that confirms that the light 1 is attached to solid support 2. In some embodiments, the indicator light illuminates power button 61.

FIG. 19A shows a schematic of assembly and disassembly of light 1 with solid support 2 via electrical connector 51. The light 1 comprising connector 60 is inserted into electrical connector 51 (panel 1). The light 1 is locked in place by turning clockwise (panel 2). The light is used (e.g. to illuminate a medical procedure table) (panel 3). The light is unlocked by turning counterclockwise (panel 3) and disassembled (panel 4).

FIG. 19B shows a close up of connector component 57. Connector component 57 comprises connector 60 comprising electrical contact 56 and insertion component 59 and electrical connector 51 comprising locking groove 58. To connect the light, insertion component 59 is inserting into electrical connector 51 and connector 60 is rotated such that a protrusion inside of the connector 60 (not shown) engages into and travels the pathway of locking groove 58. The dimensions of the components are selected such that when the connector 60 is fully rotated, the electrical connection between electrical contact 56 and electrical connector 51 is securely achieved. When locked, the electrical contacts 56 are in operable contact with electrical components (not shown) in the electrical connector 51. To disconnect the light 1, the connector 60 is rotated in the opposite direction and the connector component 57 is removed from electrical connector 51.

In some embodiments, the light is provided in a system with the solid support 2 and clamp 3. In some embodiments, solid support 2 (FIG. 3) is a rigid metal or other material (e.g. rigid plastic or resin). In some embodiments, the solid support is a single straight tube or rod or other shape. In some embodiments, the solid support comprises one or more segments. In some embodiments, one or more of the segments is rigid or flexible. In some embodiments, one or more of the segments are straight or curved or another geometry. In some embodiments, the solid support 2 is shaped and dimensioned to position the light 1 in an ideal location within the surgical field, while eliminating or minimizing interference by either the light 1 or solid support 2 with the surgeon or other medical personnel or equipment.

In some embodiments, the solid support is sterilizable (e.g., via autoclave). In some embodiments, the solid support attaches to a medical procedure surface. In some embodiments, the solid support is attaches to the medical procedure surface using clamp 3. In some embodiments, the medical procedure surface is a surgical bed (e.g., bed rail). In some embodiments, the height of the solid support is adjustable (e.g., via the clamp). For example, in some embodiments, the solid support slides through the clamp until the desired height is reached. The clamp is then tightened and the solid support is locked in place at the desired height.

In some embodiments, systems comprise one or more software components (e.g. located on the solid support or lighting components, remotely, or a combination).

In some embodiments, cameras and or microphones provided with the system survey the surgical environment and record useful information and/or provide useful feedback to the surgeon, the patient, or others. For example, in some embodiments, video and or sound information collected is sent to and evaluated by a remote user (or computer) and provides feedback to improve the procedure or to evaluate the procedure for after-procedure feedback. In some embodiments, the system monitors, via video or audio, the treating physician to identify signs of fatigue and provides a warning (e.g., alarm light or sound) to notify the physician that they should remain alert or take some other action (e.g., drink coffee, swap shifts with another physician, etc.).

In some embodiments, one or more motors are provided with the system that control movement or positioning of one or more components of the system. In some embodiments, a motor is located at the lamp and positions the direction of the lamp. In some embodiments, a motor is located in the arm portion of the lighting component, at the juncture between the lighting component and the support arm, and/or at the junction of the support arm and the table or table rail. In some embodiments, the motors are remotely controlled to control the position of one or more portions of the system. In some embodiments, the motors are controlled by a foot pedal, joystick, or other external device. In some embodiments, the system comprises a body-tracking feature that detects an object in the room and moves the light in response to movement of the object. The object may be the physician's head (e.g., eyes) (e.g., identified by video capture, a fiducial located on the physician, etc.), arms, or hands or a medical device or a location on a patient. In some preferred embodiments, head tracking is employed such that the light moves to simulate lighting that would have been provided by a headlight worn by the physician. In some embodiments, system components are automatically moved to adjust for lighting quality, avoidance of shadows at the surgical site, or other desired optimizations. In some embodiments, remote components of the system communicate wirelessly, for example, using WiFi, Bluetooth, near-field communication technology, or other protocols.

The devices and systems described herein find use in a variety of medical procedures. The lights find use in any medical procedure that utilizes a sterile field and detailed lighting. In some embodiments, the medical procedure is surgery, for example transplant surgery, although other surgeries and medical procedures are specifically contemplated.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A system, comprising:
   a) a sterile surgical light, comprising a lamp operably linked to a multi-segment flexible arm comprising two flexible sections disposed on either side of a single rigid section, wherein the total lengths of said flexible sections and said rigid section are present at a ratio of 0:2 to 2:1, wherein at least one end of said flexible arm comprises a ferrule and a connector comprising an electrical contact and an insertion component configured to insert into at least one electrical connector;
   b) a solid support configured to attach said light to a medical procedure surface using a support attachment component, wherein said solid support comprises at least two curved segments that align said surgical light over said medical procedure surface; and
   c) said at least one electrical connector configured to attached said solid support to said sterile surgical light, wherein said electrical connector comprises an electrical contact, a locking groove and an indicator light.

2. The system of claim 1, wherein said solid support is attached to said medical procedure surface using a clamp.

3. The system of claim 1, wherein said at least two curved segments comprise a first distal segment that connects to said medical procedure surface, a second segment that runs parallel to the plane of said medical procedure surface and a third, most proximal segment that attaches to said light.

4. The system of claim 3, wherein said third segment is angled between 90° and 180° relative to said second segment.

5. The system of claim 1, wherein said light further comprises a power source.

6. The system of claim 1, wherein said light further comprises a camera.

7. The system of claim 6, wherein said camera is attached to said flexible arm via a camera attachment clip.

8. The system of claim 1, wherein said lamp is focusable.

9. The system of claim 1, wherein said light further comprise an on-off switch.

10. The system of claim 9, wherein said on-off switch is located on said power source.

11. The system of claim 1, wherein said lamp comprises at least one light source.

12. The system of claim 11, wherein said lamp comprises at least two light sources, wherein each of said light sources emits light of a different wavelength or range of wavelengths.

13. The system of claim 12, wherein said light source is configured to emit pulses of light.

14. The system of claim 12, wherein said light source is configured to switch between said two light sources.

15. The system of claim 1, wherein said support attachment component is a component of said power source.

16. A method of lighting a medical procedure, comprising:
   a) contacting the system of claim 1 with a medical procedure surface; and
   b) illuminating said medical procedure surface with said light.

* * * * *